US006534479B1

(12) United States Patent
Murgita

(10) Patent No.: US 6,534,479 B1
(45) Date of Patent: *Mar. 18, 2003

(54) RECOMBINANT ALPHA-FETOPROTEIN HYBRID CYTOTOXINS FOR TREATING AND DIAGNOSING CANCERS

(75) Inventor: Robert A. Murgita, Montreal (CA)

(73) Assignee: Martinex R & D Inc., Montreal (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/758,757

(22) Filed: Dec. 3, 1996

Related U.S. Application Data

(63) Continuation of application No. 08/377,311, filed on Jan. 24, 1995, now abandoned.

(51) Int. Cl.$^7$ .......................... A61K 38/17; C07K 17/06

(52) U.S. Cl. ...................... 514/12; 530/402; 424/181.1; 424/183.1

(58) Field of Search .......................... 424/277.1, 181.1, 424/183.1; 530/402, 403; 514/12

(56) References Cited

U.S. PATENT DOCUMENTS

| | | | |
|---|---|---|---|
| 4,692,332 A | | 9/1987 | McMichael |
| 4,877,610 A | | 10/1989 | McMichael |
| 4,962,189 A | * | 10/1990 | Bloh |
| 4,966,753 A | | 10/1990 | McMichael |
| 4,970,071 A | | 11/1990 | McMichael |
| 5,130,415 A | | 7/1992 | Tecce et al. |
| 5,206,153 A | | 4/1993 | Tamaoki et al. |
| 5,965,528 A | * | 10/1999 | Murgita |
| 6,288,034 B1 | * | 9/2001 | Murgita |

FOREIGN PATENT DOCUMENTS

| | | |
|---|---|---|
| EP | 0 001 812 | 5/1979 |
| JP | 20058666 | 1/1990 |
| WO | WO 86/04241 | 7/1986 |
| WO | WO 93/05774 | 1/1993 |
| WO | WO 94/10199 | 5/1994 |

OTHER PUBLICATIONS

Bowie et al. Science 87:1306–1310, Mar. 1990.*
Kumar et al. PNAS 1306–1310, Feb. 1990.*
Lazar et al. Mol. Cell. Biol. 8(3):1247–1252, Mar. 1988.*
Burgess et al. J. Cell. Biol. 111:2129–2138, Nov. 1990.*
Salgaller et al. Cancer Immunol. Immunother. 39:105–116, 1994.*
Abramsky, et al., Journal of Neuroimmunology, 2:1–7 (1982).
Abramsky et al., Annals New York Academy of Sciences, pp. 108–115 (1983).
Aoyagi et al., Gann, 75:809–815 (1984).
Biddle et al., Breast Cancer Research and Treatment, 10:279–286 (1897).
Boismenu et al., Life Sciences, 43:673–681 (1988).
Brenner et al., Annals New York Academy of Sciences, pp. 208–221 (1981).
Brenner et al., Proc. Natl. Acad. Sci. USA, 77:3635–3639 (1980).
Brenner et al., Immunology Letters, 3:163–167 (1981).
Buamah et al., Clinica Chimica Aca., 139:313–316 (1984).
Buschman et al., Journal of Neuroimmunology 13:315–330 (1987).
Cohen et al., Scand. J. Immunol. 23:211–223 (1986).
Dattwyler et al., Nature, 256:656–657 (1975).
Gershwin et al., The Journal of Immunology, 121:2292–2298 (1978).
Glazier et al., J. Exp. Med., 158:1–8 (1983).
Goidl et al., Developmental of Immunobiology, pp. 35–55 (1979).
Hamel et al., Phenotype and Function of Bone Marrow –Derived T– and Non–T–Cells Activated In Vitro By Alpha–Fetoprotein, In: Biological Activities of Alpha$_1$–Fetoprotein (vol. I), Mizejewski, G.J. and Jacobson, H.I (eds.), CRC Press, Inc. (Boca Raton, FL), pp. 167–177 (1987).
Heyward et al., The Lancet, pp. 1161–1162 (1983).
Hooper et al., Human AFP Inhibits Cell Proliferation and NK–Like Cytotoxic Activity Generated in Autologous, But Not In Allogeneic Mixed Lymphocyte Reactions, In: Biological Activities of Alpha$_1$–Fetoprotein, (vol. II) Mizejewski, G.J. and Jacobson, H.I (eds.), CRC Press, Inc. (Boca Raton, FL), pp. 183–197 (1989).
Hooper et al., Selective Inhibition Of Murine T–Cell Proliferation And Lymphokine–Activated Natural Killer Cell Function By alpha–Fetoprotein, In: Biological Activities of Alpha$_1$–Fetoprotein, (vol. I) Mizejewski, G.J. and Jacobson, H.I (eds.), CRC Press, Inc. (Boca Raton, FL), pp. 153–165 (1987).
Hooper et al., Cellular Immunology, 63:417–425, (1981).
Hooper et al., Oncodevelopmental Biology and Medicine, 3:151–160 (1982).
Hoskin et al., Cellular Immunology, 96:163–174 (1985).
Hoskin et al., Clin. exp. Immunol., 76:262–267 (1989).
Hoskin et al., Analysis Of Pregnancy–Associated Immunoregulatory Pathways, In: Alpha–Fetoprotein and Congenital Disorders, Academic Press, New York, pp. 59–78, (1985).
Innis et al., Archives of Biochemistry and Biophysics, 195:128–135 (1979).
Ishiguro et al., Cancer, 55:156–159 (1985).
Jacobson et al., Cancer Research, 50:415–420 (1990).
Jiang et al., Science, 256:1213–1215 (1992).

(List continued on next page.)

*Primary Examiner*—Gary Kunz
*Assistant Examiner*—Stephen Gucker
(74) *Attorney, Agent, or Firm*—Clark & Elbing LLP

(57) ABSTRACT

Disclosed is a method of inhibiting a neoplasm in a mammal, the method includes administering to the mammal a therapeutically effective amount of recombinant human alpha-fetoprotein.

4 Claims, 8 Drawing Sheets

OTHER PUBLICATIONS

Figure 2:
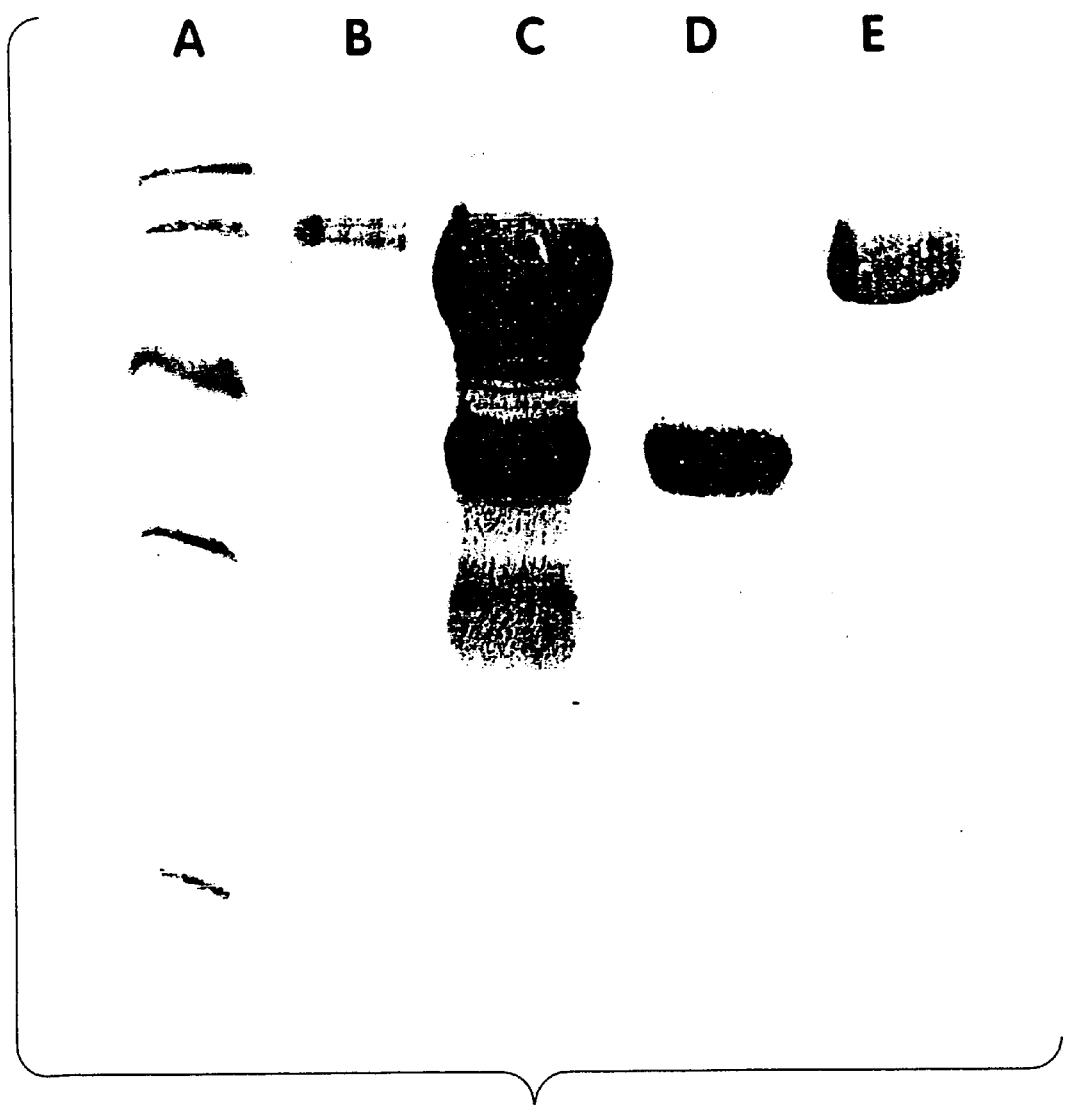

Keller et al., Immunosuppressive Properties of AFP: Role of Estrogens, In: Onco–Developmental Gene Expression, Fishman, W.H. and Sell, S. (eds.), Academic Press, Inc. (New York) pp. 287–295 (1976).
Kikutani et al., Advances in Immunology, 51:285–322 (1992).
Line et al., Medical Potential Of AFP As A Tumor Imaging Agent, In: Biological Activities of Alpha$_1$–Fetoprotein (vol. II), Mizejewski, G.J. and Jacobson, H.I (eds.), CRC Press, Inc. (Boca Raton, FL), pp. 139–148 (1989).
Lu et al., The Journal of Immunology, 132:1722–1727 (1984).
Masuda et al., Tumor Biol., 15:175–183 (1994).
Mizejewski, Gerald J., Laboratory Management, (1987).
Morinaga et al., Proc. Natl. Acad. Sci. USA, 80:4604–4608 (1983).
Moro et al., Tumor Biol., 14:116–130 (1993).
Murgita et al., La Ricerca Clin. Lab., 9:327–342 (1979).
Murgita et al., Prog. Allergy, 29:54–133 (1981).
Murgita et al., The Journal of Experimental Medicine, 141:440–452 (1975).
Murgita et al., The Journal of Experimental Medicine, 141:269–286 (1975).
Murgita et al., Proc. Natl. Acad. Sci. USA, 75:2897–2901 (1978).
Murgita et al., Clin. exp. Immunol., 33:347–256 (1978).
Murgita et al., Scand. J. Immunol., 5:1215–1220 (1976).
Murgita, Scand. J. Immunol., 5:1003–1014 (1976).
Murgita et al., Nature, 267:257–259 (1977).
Murgita et al., Eur. J. Immunol., 11:957–964 (1981).
Nelson et al., The New England Journal of Medicine, 329:466–471 (1993).
Nishi et al., J. Biochem., 104:968–972 (1988).
O'Neill et al., Oncodevelopmental Biology and Medicine, 3:135–150 (1982).
Peck et al., The Journal of Immunology, 128:1134–1140 (1982).
Peck et al., The Journal of Experimental Medicine, 147:667–683 (1978).
Peck et al., J. Exp. Med., pp. 360–372 (1978).
Sell, S., In: Cancer Markers Diagnostic and Developmental Significance, Sell, S., (ed.), Humana Press, Clifton, NJ pp. 249–293 (1980).
Semeniuk et al., Abstract 2799, Experimental Biology 94™, Anaheim, CA (1994).
Soto et al., Proc. Natl. Acad, Sci. USA, 77:2084–2087 (1980).
van Oers et al., Journal of Chromatography, 525:59–69 (1990).
van Oers, et al., J. Exp. Med., 170:811–825 (1989).
Villacampa et al., Biochemical and Biophysical Research Communications, 122:1322–1327 (1984).
Yamamoto et al., Life Sciences, 46:1679–1686 (1990).
Giuliani et al., Protein Engineering, 2:605–610 (1989).

* cited by examiner

ATTGTGCTTCCACTGCCAATAACAAAATAACTAGCAACC

```
  1                                              10
thr leu his arg asn glu tyr gly ile ala
ACA CTG CAT AGA AAT GAA TAT GGA ATA GCT 31                                              40
phe phe ala gln phe val gln glu ala thr
TTT TTT GCC CAG TTT GTT CAA GAA GCC ACT 61                                              70
asp glu gln ser ser gly cys leu glu asn
GAT GAA CAG TCT TCA GGG TGT TTA GAA AAC 91                                             100
his ser asp cys cys ser gln ser glu glu
CAT TCA GAC TGC TGC AGC CAA AGT GAA GAG 121                                             130
gln val pro glu pro val thr ser cys glu
CAA GTT CCA GAA CCT GTC ACA AGC TGT GAA 151                                             160
his pro phe leu tyr ala pro thr ile leu
CAT CCC TTC CTG TAT GCA CCT ACA ATT CTT 181                                             190
glu cys phe gln thr lys ala ala thr val
GAA TGC TTC CAA ACA AAG GCA GCA ACA GTT 211                                             220
phe gly thr arg thr phe gln ala ile thr
TTT GGG ACC CGA ACT TTC CAA GCC ATA ACT 241                                             250
leu asp val ala his val his glu his cys
CTG GAT GTG GCC CAT GTA CAT GAG CAC TGT 271                                             280
ser gln gln asp thr leu ser asn lys ile
TCT CAA CAA GAC ACT CTG TCA AAC AAA ATA 301                                             310
asp glu lys pro glu gly leu ser pro asn
GAT GAA AAA CCT GAA GGT CTA TCT CCA AAT 331                                             340
phe leu ala ser phe val his glu tyr ser
TTC TTG GCA AGT TTT GTT CAT GAA TAT TCA
```

Fig. 1A

```
                    -19
        met lys trp val glu ser ile phe leu
        ATG AAG TGG GTG GAA TCA ATT TTT TTA
                                         20
ser ile leu asp ser tyr gln cys thr ala
TCC ATA TTG GAT TCT TAC CAA TGT ACT GCA
                                         50
tyr lys glu val ser lys met val lys asp
TAC AAG GAA GTA AGC AAA ATG GTG AAA GAT
                                         80
gln leu pro ala phe leu glu glu leu cys
CAG CTA CCT GCC TTT CTG GAA GAA CTT TGC
                                        110
gly arg his asn cys phe leu ala his lys
GGA AGA CAT AAC TGT TTT CTT GCA CAC AAA
                                        140
ala tyr glu glu asp arg glu thr phe met
GCA TAT GAA GAA GAC AGG GAG ACA TTC ATG
                                        170
leu trp ala ala arg tyr asp lys ile ile
CTT TGG GCT GCT CGC TAT GAC AAA ATA ATT
                                        200
thr lys glu leu arg glu ser ser leu leu
ACA AAA GAA TTA AGA GAA AGC AGC TTG TTA
                                        230
val thr lys leu ser gln lys phe thr lys
GTT ACT AAA CTG AGT CAG AAG TTT ACC AAA
                                        260
cys arg gly asp val leu asp cys leu gln
TGC AGA GGA GAT GTG CTG GAT TGT CTG CAG
                                        290
thr glu cys cys lys leu thr thr leu glu
ACA GAA TGC TGC AAA CTG ACC ACG CTG GAA
                                        320
leu asn arg phe leu gly asp arg asp phe
CTA AAC AGG TTT TTA GGA GAT AGA GAT TTT
                                        350
arg arg his pro gln leu ala val ser val
AGA AGA CAT CCT CAG CTT GCT GTC TCA GTA
```

Fig. 1B

AT (2)

```
            -10                                              -1
            ile phe leu leu asn phe thr glu ser arg
            ATT TTC CTA CTA AAT TTT ACT GAA TCC AGA    (101)

30
            glu ile ser leu ala asp leu ala thr ile
            GAG ATA AGT TTA GCT GAC CTG GCT ACC ATA    (191)

60
            ala leu thr ala ile glu lys pro thr gly
            GCA TTG ACT GCA ATT GAG AAA CCC ACT GGA    (281)

90
            his glu lys glu ile leu glu lys tyr gly
            CAT GAG AAA GAA ATT TTG GAG AAG TAC GGA    (371)

120
            lys pro thr pro ala ser ile pro leu phe
            AAG CCC ACT CCA GCA TCG ATC CCA CTT TTC    (461)

150
            asn lys phe ile tyr glu ile ala arg arg
            AAC AAA TTC ATT TAT GAG ATA GCA AGA AGG    (551)

180
            pro ser cys cys lys ala glu asn ala val
            CCA TCT TGC TGC AAA GCT GAA AAT GCA GTT    (641)

210
            asn gln his ala cys ala val met lys asn
            AAT CAA CAT GCA TGT GCA GTA ATG AAA AAT    (731)

240
            val asn phe thr glu ile gln lys leu val
            GTT AAT TTT ACT GAA ATC CAG AAA CTA GTC    (821)

270
            asp gly glu lys ile met ser tyr ile cys
            GAT GGG GAA AAA ATC ATG TCC TAC ATA TGT    (911)

300
            arg gly gln cys ile ile his ala glu asn
            CGT GGT CAA TGT ATA ATT CAT GCA GAA AAT    (1001)

330
            asn gln phe ser ser gly glu lys asn ile
            AAC CAA TTT TCT TCA GGG GAA AAA AAT ATC    (1091)

360
            ile leu arg val ala lys gly tyr gln glu
            ATT CTA AGA GTT GCT AAA GGA TAC CAG GAG    (1181)
```

Fig. 1C

```
361                                                     370
leu leu glu lys cys phe gln thr glu asn
TTA TTG GAG AAG TGT TTC CAG ACT GAA AAC 391                                                     400
ala leu ala lys arg ser cys gly leu phe
GCA TTG GCA AAG CGA AGC TGC GGC CTC TTC 421                                                     430
pro gln leu thr ser ser glu leu met ala
CCC CAG CTG ACC TCG TCG GAG CTG ATG GCC 451                                                     460
leu ala cys gly glu gly ala ala asp ile
TTG GCC TGT GGC GAG GGA GCG GCT GAC ATT 481                                                     490
cys cys thr ser ser tyr ala asn arg arg
TGC TGC ACT TCT TCA TAT GCC AAC AGG AGG 511                                                     520
lys phe ile phe his lys asp leu cys gln
AAG TTC ATT TTC CAT AAG GAT CTG TGC CAA 541                                                     550
lys pro gln ile thr glu glu gln leu glu
AAG CCA CAA ATA ACA GAG GAA CAA CTT GAG 571                                                     580
val cys phe ala glu glu gly gln lys leu
GTC TGC TTT GCT GAA GAG GGA CAA AAA CTG
```

TTCATTCGGTGTGAACTTTTCTCTTTAATTTTAACTGA

TG(A) 10  (2039)

Fig. 1D

```
                                                    380
pro leu glu cys gln asp lys gly glu glu
CCT CTT GAA TGC CAA GAT AAA GGA GAA GAA 410
gln lys leu gly glu tyr tyr leu gln asn
CAG AAA CTA GGA GAA TAT TAC TTA CAA AAT 440
ile thr arg lys met ala ala thr ala ala
ATC ACC AGA AAA ATG GCA GCC ACA GCA GCC 470
ile ile gly his leu cys ile arg his glu
ATT ATC GGA CAC TTA TGT ATC AGA CAT GAA 500
pro cys phe ser ser leu val val asp glu
CCA TGC TTC AGC AGC TTG GTG GTG GAT GAA 530
ala gln gly val ala leu gln thr met lys
GCT CAG GGT GTA GCG CTG CAA ACG ATG AAG 560
ala val ile ala asp phe ser gly leu leu
GCT GTC ATT GCA GAT TTC TCA GGC CTG TTG 590
ile ser lys thr arg ala ala leu gly val
ATT TCA AAA ACT CGT GCT GCT TTG GGA GTT
```

TTTAACACTTTTTGTGAATTAATGAAA<u>TGATAAA</u>GACTTTTA

Fig. 1E

```
                                            390
glu leu gln lys tyr ile gln glu ser gln
GAA TTA CAG AAA TAC ATC CAG GAG AGC CAA   (1271)

420
ala phe leu val ala tyr thr lys lys ala
GCG TTT CTC GTT GCT TAC ACA AAG AAA GCC   (1361)

450
thr cys cys gln leu ser glu asp lys leu
ACT TGT TGC CAA CTC AGT GAG GAC AAA CTA   (1451)

480
met thr pro val asn pro gly val gly gln
ATG ACT CCA GTA AAC CCT GGT GTT GGC CAG   (1541)

510
thr tyr val pro pro ala phe ser asp asp
ACA TAT GTC CCT CCT GCA TTC TCT GAT GAC   (1631)

540
gln glu phe leu ile asn leu val lys gln
CAA GAG TTT CTC ATT AAC CTT GTG AAG CAA   (1721)

570
glu lys cys cys gln gly gln glu gln glu
GAG AAA TGC TGC CAA GGC CAG GAA CAG GAA   (1811)

ter
TAA   ATTACTTCAGGGGAAGAGAAGACAAAACGAGTCT   (1908)

TGTGAGATTTCCTTATCACAGAAATAAAATATCTCCAAA   (2027)
```

Fig. 1F

RECOMBINANT ALPHA-FETOPROTEIN HYBRID CYTOTOXINS FOR TREATING AND DIAGNOSING CANCERS

This is a continuation of application Ser. No. 08/377,311, filed Jan. 24, 1995, now abandoned.

BACKGROUND OF THE INVENTION

This invention relates to cancer therapeutics and diagnostic methods.

Cancer is one of the most common of all human diseases, resulting in over 500,000 deaths annually in the United States alone. Cancer typically is detected by the physician as an abnormal growth, or tumor, which causes illness by production of biochemically active molecules, by local expansion, or by invasion into neighboring or outlying tissue sites. The symptoms of the illness depend upon the specific molecular product(s) of the cancer. Thus, each type of cancer has a characteristic developmental history that describes the likely clinical course of the particular neoplastic process. For example, it is known that breast cancer spreads most frequently to the lungs, liver, bone, and brain.

Early detection and diagnosis of cancer is often necessary for devising an optimal treatment plan for a patient. By determining the presence of early metastatic disease, treatment can often be designed which increases the chance for cure, or delay the development of symptoms if a cure is not achievable. Radiographic imaging is one such procedure widely used for the detection and diagnosis of various disease states, including cancer. For example, radioactive tracers or imaging agents are used for imaging studies to detect sites of human disease. Such tracer molecules are designed to concentrate at a target and define the extent of a tumor or other disease state. Isotopes coupled to monoclonal antibodies, for example, are of clinical interest as applied to cancer screening. Imaging agents are most effective if they show a high specific localization at the target site, i.e., a high target-to-background contrast. The contrast produced by an imaging agent, e.g., a labelled monoclonal antibody, is largely determined by its biodistribution in vivo. Accordingly, to improve the ability to detect abnormalities such as cancer, the development of imaging agents specifically targeted to cancerous cells is considered essential.

As for cancer treatment, although current therapies such as surgery, biologic therapies, radiotherapies, and chemotherapies have saved and improved countless lives, they remain imperfect solutions. Indeed, a major clinical problem is that many cancers remain unresponsive to these therapies. For example, the capacity to cure disseminated cancer is dependent on combination chemotherapy, alone or together with biologic therapy, surgery, and/or radiotherapy. Moreover, many cancer cells have been found to develop resistance to many anti-cancer drugs attenuating their therapeutic effectiveness. Accordingly, the search has begun for new anti-cancer compounds which can interact with oncogene products, gene regulators, and growth factors and their receptors. Research employing the tools of molecular biology promises to provide a new array of anti-cancer agents.

SUMMARY OF THE INVENTION

In general, the invention features compositions and methods for the protection, treatment, and diagnosis of neoplasia, in particular, cancer. The invention is based on my discovery that unglycosylated recombinant human alpha-fetoprotein made in a prokaryote (e.g., E. coli) is useful for treating and diagnosing mammals with neoplasms, especially malignant tumors, such as breast or prostate carcinomas, and other carcinomas caused by a proliferation of malignant cells which express receptors which are recognized by recombinant human alpha-fetoprotein.

In one aspect, the invention features a method of inhibiting a neoplasm in a mammal (e.g., a human patient), involving administering to the mammal a therapeutically effective amount of recombinant human alpha-fetoprotein or an anti-neoplasm fragment or analog thereof. Preferably, the neoplasm is a malignant tumor (e.g., a breast tumor or a prostate tumor); and the recombinant human alpha-fetoprotein is produced in a prokaryotic cell (e.g., E. coli) and is unglycosylated. In preferred embodiments, the cells of the neoplasm express a receptor which is recognized by the recombinant human alpha-fetoprotein. Such a neoplasm is generally a carcinoma such as an adenocarcinoma or a sarcoma. In preferred embodiments, the neoplasm proliferates in response to a hormone, e.g, estrogen or androgen. Preferably, administration of recombinant human alpha-fetoprotein inhibits the proliferation of cells of the neoplasm or, alternatively, kills cells of the neoplasm in the mammal. The method further includes administering to the mammal a chemotherapeutic agent.

In another aspect, the invention features a method of protecting a mammal from developing a neoplasm, involving administering to the mammal a therapeutically effective amount of recombinant human alpha-fetoprotein. Preferably, the recombinant human alpha-fetoprotein is produced in a prokaryotic cell (e.g., E. coli) and is unglycosylated.

In another aspect, the invention features a hybrid cytotoxin including a recombinant human alpha-fetoprotein (or a fragment or analog thereof) linked to a cytotoxic agent. Examples of such cytotoxic agents include, without limitation, diphtheria toxin, Pseudomonas exotoxin A; ricin and other plant toxins such as abrin, modeccin, volkensin, viscumin; chlorea toxin (produced by Vibrio cholerae bacteria); the so-called "Shiga-like" toxins (produced by E. coli and other enteric bacteria); Salmonella heat-labile enterotoxin; and E. coli heat-labile enterotoxin. In other preferred embodiments, the cytotoxic agent is non-proteinaceous. Examples of such non-proteinaceous cytotoxic agents include, without limitation, anti-cancer agents such as doxorubicin, as well as α-emitting radionuclides such as astatine and β-emitting nuclides such as yttrium. Preferably, the cytotoxic agent of the hybrid cytotoxin is linked by a peptide bond to the recombinant human alpha-fetoprotein, and the hybrid toxin is produced by expression of a genetically engineered hybrid DNA molecule. In other preferred embodiments, the cytotoxic agent of the hybrid cytotoxin is a protein; such a cytotoxic agent is chemically conjugated to the recombinant human alpha-fetoprotein.

In other aspects, the invention features a detectably-labelled recombinant human alpha-fetoprotein or a detectably-labelled fragment or analog thereof capable of binding to a human neoplastic cell. Preferably such a molecule is labelled with a radionuclide, e.g., technetium-99 m, iodine-125, iodine-131, or indium. Other detectable labels include, without limitation, enzymes, fluorophores, or other moieties or compounds which emit a detectable signal (e.g., radioactivity, fluorescence, color) or emit a detectable signal after exposure of the label to its substrate or, alternatively, the detectable signal can be an epitope recognized by an antibody (e.g., an epitope of alpha-fetoprotein or an epitope which is specifically engineered into the recombinant alpha-fetoprotein such as the HA or myc epitopes). Preferably, the molecule targets a malignant tumor (e.g. a breast tumor, a prostate tumor, or a carcinoma) which express a receptor which is recognized by the recombinant alpha-fetoprotein (or fragment or analog thereof). Typically, such recombinant alpha-fetoprotein is produced in a prokaryotic cell (e.g., *E. coli*) and is unglycosylated.

Detectably-labelled recombinant human alpha-fetoprotein is useful for methods of imaging a neoplastic cell-containing region in a human patient in vivo. In general, the method involves: (a) providing a detectably-labelled molecule of recombinant human alpha-fetoprotein (or a fragment or analog thereof); (b) administering the molecule to the patient; (c) allowing the labelled molecule to bind and allowing unbound molecule to be cleared from the region; and (d) obtaining an image of the neoplastic cell-containing region. Preferably, the region is the breast or is the prostate. In other preferred embodiments, the region, without limitation, is liver tissue, is lung tissue, is spleen tissue, is pancreatic tissue, is brain tissue, is lymph tissue, or is bone marrow. Preferably, the image is obtained using dynamic gamma scintigraphy.

Detectably-labelled recombinant human alpha-fetoprotein (or fragment or analog thereof) can also be used in a method for diagnosing a neoplasm in a mammal (e.g., a human patient). Such a method includes: (a) contacting the biological sample with the detectably-labelled molecule of recombinant human alpha-fetoprotein; and (b) detecting the label bound to the sample, where the detection of label above background levels is indicative that the patient has a neoplasm. Preferably, the method involves a biological sample including cells fixed and sectioned prior to the contacting step, and the label bound to the sample is bound to areas corresponding to the cell membrane of the cells. In preferred embodiments, the biological sample is from the breast or prostate of a human patient.

Detectably-labelled recombinant human alpha-fetoprotein (or fragment or analog thereof) can also be used in a method for detecting a neoplasm a mammal in vivo. Such a method includes: (a) administering a diagnostically effective amount of the detectably-labelled molecule of recombinant human alpha-fetoprotein; and (c) detecting the presence of the detectable label bound to a tissue of the mammal, where an amount of label above background levels is indicative of the presence of the neoplasm in the mammal. In preferred embodiments, the method involves a human patient suspected of having a breast cancer, and the tissue is breast tissue. In other preferred embodiments, the method involves a human patient suspected of having a prostate cancer, and the tissue is prostate tissue. Preferably, the detectably labelled recombinant human alpha-fetoprotein is linked to a radionuclide (e.g., technetium-90) and the detection step is accomplished by radioimaging (e.g., dynamic gamma scintigraphy).

In another aspect, the invention features kits for detecting a neoplasm or any cell expressing a receptor which is recognized by recombinant human alpha-fetoprotein (or a fragment or analog thereof) in vivo, in situ or in vitro. In general, the kits include a recombinant human alpha-fetoprotein which is recognized by a neoplasm, and which may be detectably labeled. If the recombinant human alpha-fetoprotein is unlabelled, a second reagent containing a detectable label (e.g. a radionuclide such as technetium-90, iodine-125, iodine-131, or indium) is preferably included. Where the detectable label is an enzyme, the kit further includes a substrate reagent for the enzyme. The kit may also include a reagent for linking the detectable label to the recombinant alpha-fetoprotein. In another embodiment, the kit for detecting a neoplasm or any unwanted cell expressing a receptor which is recognized by recombinant human alpha-fetoprotein (or a fragment or analog thereof) includes a reagent containing an antibody which specifically binds the recombinant human alpha-fetoprotein and a reagent including a detectably labeled recombinant human alpha-fetoprotein that is specifically bound by the anti-alpha-fetoprotein antibody. Preferably, the recombinant human alpha-fetoprotein of the kit is produced in a prokaryotic cell (*E. coli*) and is unglycosylated.

By "neoplasm" is meant any unwanted growth of cells serving no physiological function. In general, a cell of a neoplasm has been released from its normal cell division control, i.e., a cell whose growth is not regulated by the ordinary biochemical and physical influences in the cellular environment. In most cases, a neoplastic cell proliferates to form a clone of cells which are either benign or malignant. Examples of neoplasms include, without limitation, transformed and immortalized cells, tumors, and carcinomas such as breast cell carcinomas and prostate carcinomas.

By "therapeutically effective amount" is meant a dose of unglycosylated recombinant human alpha-fetoprotein or an anti-neoplasm fragment or analog thereof capable of inhibiting the proliferation of a neoplasm.

By "diagnostically effective amount" is meant a dose of detectably-labelled recombinant human alpha-fetoprotein or a detectably-labelled fragment or analog thereof that can be detected within a targeted region in a mammal (e.g., a human patient).

By "recombinant human alpha-fetoprotein" is meant a polypeptide having substantially the same amino acid sequence as the protein encoded by the human alpha-fetoprotein gene as described by Morinaga et al., *Proc. Natl. Acad. Sci., USA* 80: 4604 (1983). The method of producing recombinant human alpha-fetoprotein in a prokaryotic cell is described in U.S. Pat. No. 5,384,250.

The use of recombinant human alpha-fetoprotein for the treatment and diagnosis of cancer offers a number of advantages. For example, rHuAFP can be administered directly to a tumor site. Recombinant HuAFP can also be chemically defined and synthesized, and prepared in large quantities using the techniques of recombinant DNA. Moreover, unlike conventional cancer chemotherapies and radiotherapies, recombinant human alpha-fetoprotein causes minimal side effects such as nausea, vomiting, and neurotoxicity. Accordingly, relatively high doses of rHuAFP can be safely administered.

The diagnostic methods of the invention are advantageous since in that they allow for rapid and convenient diagnosis of a neoplasm. For example, the use of rHuAFP as a diagnostic agent (e.g., by radioimaging using scintigraphy) is especially advantageous for real time imaging of cancer in both pre-surgical or intraoperative localization and staging of a cancer, e.g., breast cancer, as well as during post-surgical examinations. Using such diagnostic procedures permits non-invasive determination of the presence, location, or absence of a neoplasm which is advantageous for monitoring the condition of a patient.

Other features and advantages of the invention will be apparent from the following description of the preferred embodiments thereof, and from the claims.

DETAILED DESCRIPTION

The drawings will first be described.

DRAWINGS

FIG. 1 is the nucleotide sequence (SEQ ID NO: 1) and deduced amino acid sequence (SEQ ID NO: 2) of the cDNA encoding human alpha-fetoprotein.

FIG. 2 is the SDS-PAGE analysis of rHuAFP Fragment I (SEQ ID NO: 8) (Lane A, MW marker; Lane B, natural human alpha-fetoprotein (AFP); Lane C, unpurified rHuAFP; Lane D, rHuAFP Fragment I, and Lane E, rHuAFP (amino acids 1–590 of FIG. 1, SEQ ID NO: 2).

Figure 3:
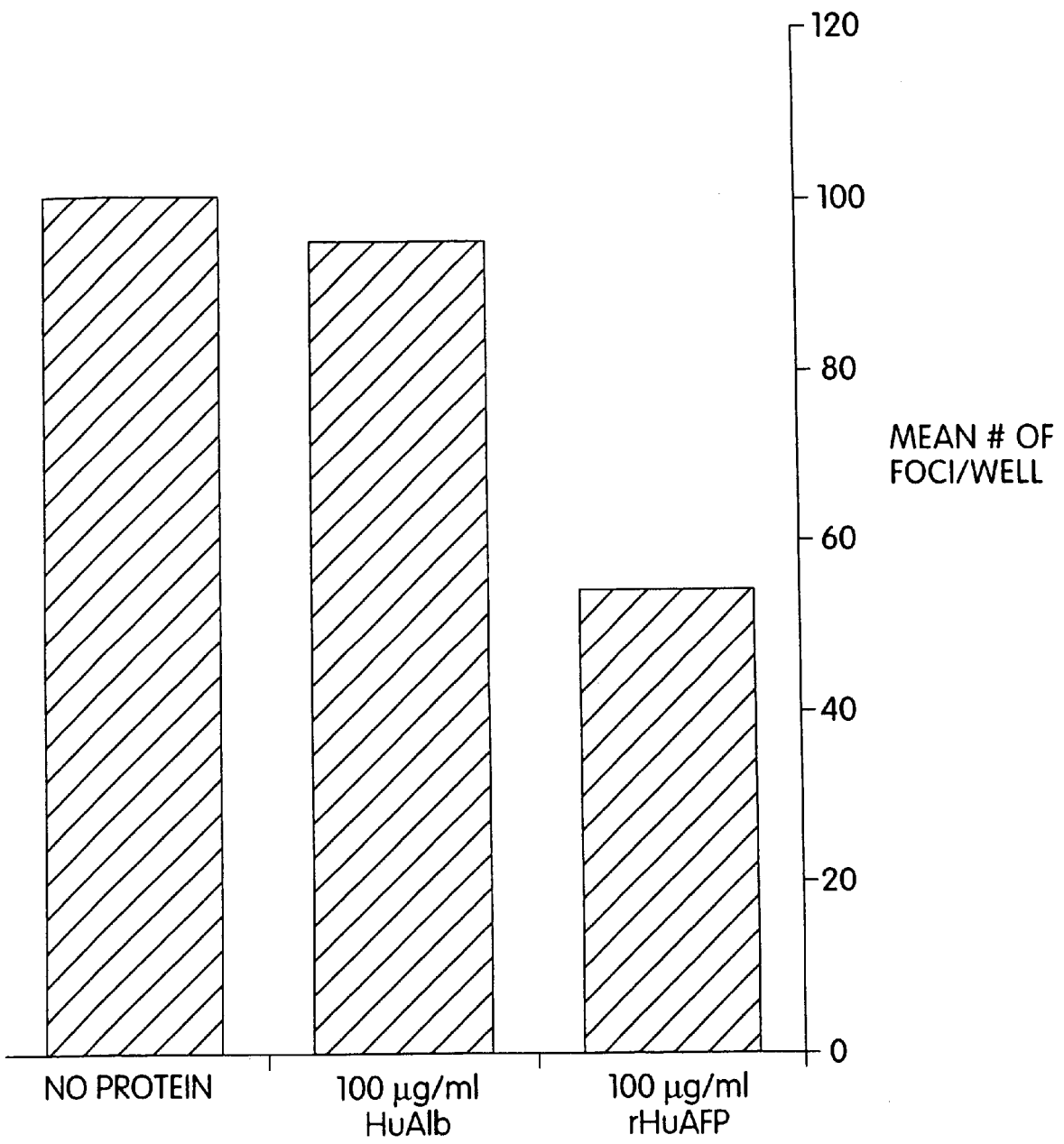

FIG. 3 is a bar graph showing the effect of rHuAFP on estrogen-stimulated post-confluent growth of MCF-7 breast cancer cells.

There now follows a detailed description of methods and compounds of the invention.

Production of Recombinant Human Alpha-Fetoprotein of the Invention

As summarized above, the invention provides compositions for therapies and diagnostic methods for the prevention and treatment of a neoplasm, involving the use of rHuAFP or anti-neoplasm fragments or analogs thereof. Methods for producing such rHuAFP in a prokaryotic cell are described in U.S. Pat. No. 5,384,250. The invention further provides such rHuAFP (or a fragment or analog thereof) linked to a toxin or a detectable label for use as anti-cancer or diagnostic agents, respectively. Production of such fragments and analogs of rHuAFP, as well as anti-cancer and diagnostic agents of rHuAFP, will now be discussed in greater detail.

Fragments and Analogs

The invention includes biologically active fragments of rHuAFP. A biologically active fragment of rHuAFP is one that possesses at least one of the following activities: (a) directs a specific interaction with a target cell, e.g., binds to a cell expressing a receptor which is recognized by rHuAFP (e.g., the membrane of a cancer cell such as an MCF-7); or (b) halts, reduces, or inhibits the growth of a neoplasm (e.g., binds to a cell surface receptor and imparts an anti-proliferative signal). The ability of rHuAFP fragments or analogs to bind to a receptor which is recognized rHuAFP can be tested using any standard binding assay known in the art.

Accordingly, a rHuAFP fragment, like the full-length rHuAFP molecule, can be used as a targeting agent for a toxin (for therapy) or a detectable compound (for diagnosis). Recombinant HuAFP fragments that effectively target a toxin or act as detectable compounds to label a cell expressing a receptor which is recognized by rHuAFP or a fragment or analog thereof are useful in the invention.

In general, fragments of rHuAFP are produced according to the techniques of polypeptide expression and purification described in U.S. Pat. No. 5,384,250. For example, suitable fragments of rHuAFP can be produced by transformation of a suitable host bacterial cell with part of an HuAFP-encoding cDNA fragment (e.g., the cDNA described above) in a suitable expression vehicle. Alternatively, such fragments can be generated by standard techniques of PCR and cloned into the expression vectors (supra). Accordingly, once a fragment of rHuAFP is expressed, it may be isolated by various chromatographic and/or immunological methods known in the art. Lysis and fractionation of rHuAFP-containing cells prior to affinity chromatography may be performed by standard methods. Once isolated, the recombinant protein can, if desired, be further purified, e.g., by high performance liquid chromatography (see, e.g., Fisher, *Laboratory Techniques In Biochemistry And Molecular Biology*, Work and Burdon, eds., Elsevier, 1980).

A rHuAFP fragment may also be expressed as a fusion protein with maltose binding protein produced in *E. coli*. Using the maltose binding protein fusion and purification system (New England Biolabs, Beverly, Mass.), the cloned human cDNA sequence can be inserted downstream and in frame of the gene encoding maltose binding protein (malE), and the malE fusion protein can then be overexpressed. In the absence of convenient restriction sites in the human cDNA sequence, PCR can be used to introduce restriction sites compatible with the vector at the 5' and 3' end of the cDNA fragment to facilitate insertion of the cDNA fragment into the vector.

Following expression of the fusion protein, it can be purified by affinity chromatography. For example, the fusion protein can be purified by virtue of the ability of the maltose binding protein portion of the fusion protein to bind to amylose immobilized on a column.

To facilitate protein purification, the pMalE plasmid contains a factor Xa cleavage site upstream of the site into which the cDNA is inserted into the vector. Thus, the fusion protein purified as described above can then be cleaved with factor Xa to separate the maltose binding protein from a fragment of the recombinant human cDNA gene product. The cleavage products can be subjected to further chromatography to purify rHuAFP from the maltose binding protein. Alternatively, a fragment of rHuAFP may be expressed as a fusion protein containing a polyhistidine tag can be produced. Such an alpha-fetoprotein fusion protein may then be isolated by binding of the polyhistidine tag to an affinity column having a nickel moiety which binds the polyhistidine region with high affinity. The fusion protein may then be eluted by shifting the pH within the affinity column. The rHuAFP can be released from the polyhistidine sequences present in the resultant fusion protein by cleavage of the fusion protein with specific proteases.

Recombinant HuAFP fragment expression products (e.g., produced by any of the prokaryotic systems described in U.S. Pat. No. 5,384,250) may be assayed by immunological procedures, such as Western blot, immunoprecipitation analysis of recombinant cell extracts, or immunofluorescence (using, e.g., the methods described in Ausubel et al., *Current Protocols In Molecular Biology*, Greene Publishing Associates and Wiley Interscience (John Wiley & Sons), New York, 1994).

Once a fragment of rHuAFP is expressed, it is isolated using the methods described supra. Once isolated, the fragment of rHuAFP can, if desired, be further purified by using the techniques described supra. Fragments can also be produced by chemical synthesis (e.g., by the methods described in *Solid Phase Peptide Synthesis*, 2nd ed., 1984, The Pierce Chemical Co., Rockford, Ill.). The ability of a candidate rHuAFP fragment to exhibit a biological activity of alpha-fetoprotein is assessed by methods known to those skilled in the art (e.g., those described herein).

The purified recombinant gene product or fragment thereof can then be used to raise polyclonal or monoclonal antibodies against the human recombinant alpha-fetoprotein using well-known methods (see Coligan et al., eds., *Current Protocols in Immunology*, 1992, Greene Publishing Associates and Wiley-Interscience). To generate monoclonal antibodies, a mouse can be immunized with the recombinant protein, and antibody-secreting B cells isolated and immortalized with a non-secretory myeloma cell fusion partner. Hybridomas are then screened for production of recombinant human alpha-fetoprotein (or a fragment or analog thereof)-specific antibodies and cloned to obtain a homogenous cell population which produces monoclonal antibodies.

As used herein, the term "fragment," as applied to a rHuAFP polypeptide, is preferably at least 20 contiguous amino acids, preferably at least 50 contiguous amino acids, more preferably at least 100 contiguous amino acids, and most preferably at least 200 to 400 or more contiguous amino acids in length. Fragments of rHuAFP molecules can be generated by methods known to those skilled in the art, e.g., proteolytic cleavage or expression of recombinant peptides, or may result from normal protein processing (e.g., removal of amino acids from nascent polypeptide that are not required for biological activity).

Recombinant HuAFP fragments of interest include, but are not limited to, Domain I (amino acids 1 (Thr)-197 (Ser), see FIG. 1, SEQ ID NO: 3), Domain II (amino acids 198 (Ser)-389 (Ser), see FIG. 1, SEQ ID NO: 1), Domain III (amino acids 390 (Gln)-590 (Val), see FIG. 1, SEQ ID NO: 5), Domain I+II (amino acids 1 (Thr)-389 (Ser), see FIG. 1, SEQ ID NO: 6), Domain II+III (amino acids 198 (Ser) -590 (Val), see FIG. 1, SEQ ID NO: 7), and rHuAFP Fragment I (amino acids 266 (Met)-590 (Val), see FIG. 1, SEQ ID NO: 8). Activity of a fragment is evaluated experimentally using conventional techniques and assays, e.g., the assays described herein.

The invention further includes analogs of full-length rHuAFP or fragments thereof. Analogs can differ from rHuAFP by amino acid sequence differences, or by modifications (e.g., post-translational modifications) which do not affect sequence, or by both. Analogs of the invention will generally exhibit at least 80%, more preferably 85%, and most preferably 90% or even 99% amino acid identity with all or part of a rHuAFP amino acid sequence. Modifications (which do not normally alter primary sequence) include in vivo, or in vitro chemical derivatization of polypeptides, e.g., acetylation, or carboxylation; such modifications may occur during polypeptide synthesis or processing or following treatment with isolated modifying enzymes. Analogs can also differ from the naturally occurring rHuAFP by alterations in primary sequence, for example, substitution of one amino acid for another with similar characteristics (e.g., valine for glycine, arginine for lysine, etc.) or by one or more non-conservative amino acid substitutions, deletions, or insertions which do not abolish the polypeptide's biological activity. These include genetic variants, both natural and induced (for example, resulting from random mutagenesis by irradiation or exposure to ethanemethylsulfate or by site-specific mutagenesis as described in Sambrook et al., *Molecular Cloning: A Laboratory Manual*, 2nd ed., Cold Spring Harbor Press, 1989,. or Ausubel et al., supra)). Also included are cyclized peptide molecules and analogs which contain residues other than L-amino acids, e.g., D-amino acids or non-naturally occurring or synthetic amino acids, e.g., β or γ amino acids, or L-amino acids with non-natural side chains (see e.g., Noren et al., *Science* 244:182, 1989). Methods for site-specific incorporation of non-natural amino acids into the protein backbone of proteins is described, e.g., in Ellman et al., *Science* 255:197, 1992. Also included are chemically synthesized polypeptides or peptides with modified peptide bonds (e.g., non-peptide bonds as described in U.S. Pat. Nos. 4,897,445 and 5,059,653) or modified side chains to obtain the desired pharmaceutical properties as described herein. Useful mutants and analogs are identified using conventional methods, e.g., those described herein.

The cloning, expression, isolation and characterization of exemplary rHuAFP fragments now follows. These examples are provided to illustrate, not limit, the invention.

Experimental

Materials and Methods

Polymerase Chain Reaction (PCR) rHuAFP Fragments

Plasmid constructs encoding fragments of human alpha-fetoprotein were prepared using polymerase chain reaction (PCR) techniques known to those skilled in the art of molecular biology, using oligonucleotide primers designed to amplify specific portions of the human alpha-fetoprotein gene (see e.g., *PCR Technology*, H. A. Erlich, ed., Stockton Press, New York, 1989; *PCR Protocols: A Guide to Methods and Applications,* M. A. Innis, David H. Gelfand, John J. Sninsky, and Thomas J. White,, eds., Academic Press, Inc., New York, 1990, and Ausubel et. al., supra).

The following six rHuAFP fragments were prepared to evaluate their biological activity (e.g., according to the methods disclosed herein):

| | | |
|---|---|---|
| Domain I | Amino acids 1 (Thr) - 197 (Ser), | (FIG. 1, SEQ ID NO: 3) |
| Domain II | Amino acids 198 (Ser) - 389 (Ser), | (FIG. 1, SEQ ID NO: 4) |
| Domain III | Amino acids 390 (Gln) - 590 (Val), | (FIG. 1, SEQ ID NO: 5) |
| Domain I + II | Amino acids 1 (Thr) - 389 (Ser), | (FIG. 1, SEQ ID NO: 6) |
| Domain II + III | Amino acids 198 (Ser) - 590 (Val), | (FIG. 1, SEQ ID NO: 7) |
| rHuAFP Fragment I | Amino acids 266 (Met) - 590 (Val), | (FIG. 1, SEQ ID NO: 8) |

Amino acids sequences were deduced from those shown for human alpha-fetoprotein (1(Thr)-590 (Val); SEQ ID NO: 2) in FIG. 1. Fragments of rHuAFP designated Domain I, Domain II, Domain III, Domain I+II, Domain II+III and rHuAFP Fragment I were synthesized using standard PCR reaction conditions in 100 μL reactions containing 34 μL H₂O, 10 μL 10× reaction buffer, 20 μL 1 mM dNTP, 2 μL DNA template (HuAFP cloned in pI18), appropriate 5' and 3' oligonucleotide primers (10 μL 10 pmol/μL 5' primer, 10 μL 10 pmol/μL 3' primer), 1 μL glycerol, 10 μL DMSO, and 1 μL Pfu polymerase (Stratagene, LaJolla, Calif.). Primers used for PCR amplifications were:

```
DomI25              5'-AAAAAAGGTACCACACTGCATAGAAATGAA-3'    (SEQ ID NO:  9)
DomI3               5'-AAAAAAGGATCCTTAGCTTTCTCTTAATTCTTT-3' (SEQ ID NO: 10)
DomII5              5'-AAAAAAATCGATATGAGCTTGTTAAATCAACAT-3' (SEQ ID NO: 11)
DomII3              5'-AAAAAAGGATCCTTAGCTCTCCTGGATGTATTT-3' (SEQ ID NO: 12)
DomIII5             5'-AAAAAAATCGATATGCAAGCATTGGCAAAGCGA-3' (SEQ ID NO: 13)
DomIII3             5'-AAAAAAGGATCCTTAAACTCCCAAAGCAGCACG-3' (SEQ ID NO: 14)
5'rHuAFP Fragment I 5'-AAAAAAATCGATATGTCCTACATATGTTCTCAA-3' (SEQ ID NO: 15)
```

Accordingly, primer pairs DomI25 and DomI3, DomII5 and DomII3, DomIII5 and DomIII3, 5'rHuAFP Fragment I and DomIII3, DomI25 and DomII3, and DomII5 and DomIII3 were used to isolate cDNA sequences of Domain I, Domain II, Domain III, rHuAFP Fragment I, Domain I+II, and Domain II+III, respectively, of rHuAFP. Annealing, extension, and denaturation temperatures were 50° C., 72° C., and 94° C., respectively, for 30 cycles. PCR products were purified according to standard methods. Purified PCR products encoding Domain I and Domain I+II were digested individually with KpnI and BamHI and cloned separately into KpnI/BamHI-treated pTrp4. Purified PCR products encoding Domain II, Domain III, Domain II+III, and rHuAFP Fragment I were digested individually with Bsp106I and BamHI and were cloned separately into Bsp106I/BamHI-treated pTrp4. Each plasmid construct was subsequently transformed into competent *E. coli cells*. Since the expression product will begin with the amino acid sequence encoded by the translation start signal methionine, it is expected that such signal will be removed, or in any event, not affect the bioactivity of the ultimate expression product.

Results

Expression and Purification

*E. coli* containing the expression plasmid encoding rHuAFP Fragment I was cultured and purified. FIG. 2 (lane D) shows the SDS-PAGE profile of the purified rHuAFP Fragment I. N-terminal amino acid sequence analysis showed that rHuAFP Fragment I possessed the amino acid sequence $Ser_{267}$-Tyr-Ile-Cys-Ser-Gln-Gln-Asp-$Thr_{275}$ (SEQ ID NO: 16) which corresponds to the expected N-terminal amino acid sequence of rHuAFP Fragment I (see FIG. 1, SEQ ID NO: 8) where the initiating methionine is cleaved intracellularly.

Cytotoxic Agents

A hybrid cytotoxin of rHuAFP is prepared by conjugating a full-length rHuAFP or a fragment or analog thereof to any number of known toxic entities using conventional techniques. Such toxins are useful for inhibiting the development of a neoplasm (as described infra). Useful cytotoxins are preferably significantly cytotoxic only when present intracellularly and are substantially excluded from any given cell in the absence of a targeting domain. As described below, peptide toxins fulfill both of these criteria and are readily incorporated into hybrid molecules. If desired, a mixed cytotoxin (i.e., a cytotoxin composed of all or part of two or more toxins) can also be used. Several useful toxins are described in more detail below.

Toxin molecules useful in the method of the invention are preferably toxins, such as peptide toxins, which are significantly cytotoxic only when present intracellularly of course, under these circumstances the molecule must be able to enter a cell bearing the targeted receptor. This ability depends on the nature of the molecule and the nature of the cell receptor. For example, cell receptors which naturally allow uptake of a ligand are likely to provide a means for a molecule which includes a toxin to enter a cell bearing that receptor. As is discussed below, the peptide toxin useful in the methods of the invention is fused to a rHuAFP (or fragment or analog thereof) binding domain by producing a recombinant DNA molecule which encodes a hybrid protein molecule.

Many peptide toxins have a generalized eukaryotic receptor binding domain; in these instances the toxin must be modified to prevent intoxication of non-receptor bearing cells. Any such modifications must be made in a manner which preserves the cytotoxic functions of the molecule (see U.S. Department of Health and Human Services, U.S. Ser. No. 401,412). Potentially useful toxins include, but are not limited to: cholera toxin, ricin, 0-Shiga-like toxin (SLT-I, SLT-II, SLT $II_v$), LT toxin, C3 toxin, Shiga toxin, pertussis toxin, tetanus toxin, Pseudomonas exotoxin, saporin, modeccin, and gelanin.

The cytotoxic portion of some molecules useful in the invention, if desired, can be provided by a mixed toxin molecule. A mixed toxin molecule is a molecule derived from two different polypeptide toxins. Generally, as discussed above, polypeptide toxins have, in addition to the domain responsible for generalized eukaryotic cell binding, an enzymatically active domain and a translocation domain. The binding and translocation domains are required for cell recognition and toxin entry respectively. The enzymatically active domain is the domain responsible for cytotoxic activity once the molecule is inside a cell.

Naturally-occurring proteins which are known to have a translocation domain include diphtheria toxin, Pseudomonas exotoxin A, and possibly other peptide toxins. The translocation domains of diphtheria toxin and Pseudomonas exotoxin A are well characterized (see, e.g., Hoch et al., *Proc. Natl. Acad. Sci. USA* 82:1692, 1985; Colombatti et al., *J. Biol. Chem.* 261:3030, 1986; and Deleers et al., *FEBS Lett.* 160:82, 1983), and the existence and location of such a domain in other molecules may be determined by methods such as those employed by Hwang et al. Cell 48:129, 1987); and Gray et al. *Proc. Natl. Acad. Sci. USA* 81:2645, 1984).

For example, one useful rHuAFP/mixed toxin hybrid molecule is formed by fusing the enzymatically active A subunit of *E. coli* Shiga-like toxin (see, e.g., Calderwood et al., *Proc. Natl. Acad. Sci. USA* 84:4364, 1987) to the translocation domain (amino acid residues 202 through 460) of diphtheria toxin, and to rHuAFP. The rHuAFP portion of the three-part hybrid causes the molecule to attach specifically to cells bearing receptors which is recognized by rHuAFP, and the diphtheria toxin translocation portion acts to insert the enzymatically active A subunit of the Shiga-like toxin into the targeted cell. The enzymatically active portion of Shiga-like toxin, like diphtheria toxin, acts on the protein synthesis machinery of the cell to prevent protein synthesis, thus killing the cell.

Functional components of the hybrid cytotoxins of the invention are linked together via a non-covalent or covalent bond, or both. Non-covalent interactions can be ionic, hydrophobic, or hydrophilic, such as interactions involved in a leucine-zipper or antibody-protein G interaction (see, e.g., Derrick et al., *Nature* 359:752, 1992). An example of a covalent linkage is a disulfide bond.

A hybrid cytotoxin is prepared by chemically conjugating rHuAFP (or fragment or analog) to a any number of known toxic entities, e.g., those described above. Such reactions are carried out by standard techniques known to those skilled in the art. A typical way of conjugating a protein to a protein toxin (including, e.g., bacterial toxins such as diphtheria toxin or Pseudomonas exotoxin A, or plant toxins such as ricin) is by crosslinking through a disulfide bond (see, e.g., Chang et al., *J. Biol. Chem.* 252:1515, 1977) or a heterobifunctional molecule (see, e.g., Cawley et al. *Cell* 22:563, 1980). See also Stevens et al., U.S. Pat. No. 4,894,227.

Alternatively, the hybrid cytotoxin is prepared by expression of a hybrid DNA engineered to encode both the rHuAFP (or a fragment or analog thereof) and the toxin (or a toxic portion thereof), using technology available to those of ordinary skill in the art of making such hybrids (see, e.g., Murphy, U.S. Pat. No. 4,675,382, and Chadhary et al., *Proc. Natl. Acad. Sci. USA* 84:4538, 1987). For example, a recombinant fusion protein of rHuAFP and a cytotoxic agent is made according to methods known in the art (see, e.g., Murphy supra and Huston et al., *Meth. Enzymol.* 203:46, 1991). If the hybrid cytotoxin is produced by expression of a fused gene, a peptide bond serves as the link between the cytotoxic agent and the targeting ligand. Another method useful for conjugating a protein or polypeptide to a protein toxin employs the polymer, monomethoxy-polyethylene glycol (mPEG), as described in Maiti et al., *Int. J. Cancer Suppl.* 3:17, 1988.

If desired, following its synthesis, the hybrid cytotoxin is affinity purified according to standard methods using antibodies against the targeting portion of the molecule, e.g., antibodies against human alpha-fetoprotein. Similarly, antibodies directed against the cytotoxic agent are also useful for purifying the hybrid cytotoxin molecule by standard immunological techniques. The resulting hybrid cytotoxin is then formulated for use as an agent against unwanted cells, e.g. cancer cells, following procedures standard in the field of pharmacology.

Molecules of the invention can be screened for the ability to decrease viability of cells bearing the targeted receptor by means of assays known in the art, e.g., those methods described herein.

Because hybrid cytotoxins of the invention are potent cytotoxic agents for cells bearing the a receptor which is recognized by rHuAFP, rHuAFP is useful in the treatment of diseases involving unwanted alpha-fetoprotein receptor-positive cells, e.g., cancer cells.

Diagnostic Agents

Recombinant rHuAFP or a fragment or analog thereof can be attached to a detectable label to produce an agent useful for detecting and localizing a neoplasm in vivo, in situ, or in vitro. Methods for attaching such labels to proteins are known in the art. For example, a detectable label is attached by chemical conjugation, but where the label is a polypeptide, it could alternatively be attached by genetic engineering techniques.

Detectable labels are generally selected from a variety of such labels known in the art, but are normally radioisotopes, flurophores, enzymes (e.g., horseradish peroxidase), or other moieties or compounds which emit a detectable signal (e.g., radioactivity, fluorescence, color) or emit a detectable signal after exposure of the label to its substrate. Various detectable label/substrate pairs (e.g., horseradish peroxidase/ diaminobenzidine, avidin/streptavidin, luciferase/luciferin, $\beta$-galactosidase/X-gal(5-Bromo-4-Chloro-3-Indoyl-D-Galactopyranoside), and methods for labelling proteins for such detection purposes are known in the art. The usefulness of such an agent can be assayed, for example, by implanting a tumor cell line, e.g, MCF-7, into a host, e.g., a mouse, and determining whether the agent of the invention detectably labels the tumor produced by such implanted cells, e.g., by radioimaging using scintigraphy. Such an agent can also be used to assay for the presence of any unwanted cell bearing an alpha-fetoprotein receptor, e.g., by using Western blot analysis or histochemical staining of a tissue sample, according to known methods.

Recombinant HuAFP as an Anti-Cancer Agent

Anti-cancer agents of the invention (e.g., rHuAFP or a fragment or analog thereof; or a hybrid cytotoxin of rHuAFP) are useful for inhibiting a neoplasm, e.g., breast or prostate carcinomas. Those skilled in the art will understand that any number of methods, both in vitro and in vivo, are used to determine the efficacy of anti-cancer agents useful in the methods of the invention. For example, the reduction of tumor growth can be monitored in a mouse or rat growing a prostate cancer (e.g., tumor xenografts of LNCaP androgen receptor-positive human prostate cancer cell line) following the administration of the test compound. In a working example, a human tumor cell lines (e.g., cell lines such as MCF-7(ATCC HTB 22), T-47D (ATCC HTB 133), MDA-MB-231 (ATCC HTB 26), BT-20 (ATCC HTB 19), NIH:OV-CAR-3 (ATCC HTB 161), LnCaP.FGC (ATCC CRL 1740), and Du-145 (ATCC HTB 81) growing in culture is released from monolayer by trypsinization, diluted into single-cell suspension and then solidified by centrifugation into a pellet which IS subsequently exposed to 15 $\mu$l fibrinogen (50 mg/ml) and 10 $\mu$l thrombin (50 units/ml) for 30 minutes at 37° C. Fibrin clots containing tumor are then cut into pieces approximately 1.5 mm in diameter. Each piece of tumor is subsequently implanted under the kidney capsule of a mouse according to standard methods. If desired, mice can be immunosuppressed by daily subcutaneous (s.c.) injection of 60 mg/kg cyclosporine A (Sandimmune IV) beginning immediately prior to tumor implantation according to conventional methods. If necessary, estrogen and androgen supplementation of mice is achieved by standard methods, e.g, implantation of silastic tubing containing estradiol or by injection of testosterone propionate. Typically, hormone supplementation is commenced on the day of tumor implantation. Generally, administration of the test molecule is initiated prior to tumor implantation and/or after tumor implantation. Control animals receive a placebo, e.g., human serum albumin or diluent, similarly administered as for rHuAFP or related molecules. The effect of the test molecule on tumor growth is monitored according to any standard method. For example, tumor growth is monitored by weekly measurement of tumor size by laparotomy using a dissecting microscope equipped with an ocular micrometer. A molecule shown experimentally to halt or reduce or inhibit the growth of such implanted tumors is considered useful in the invention.

Toxicity of test compounds towards cells bearing receptors that are recognized by rHuAFP can be tested in vitro according to any standard protocol. For example, a cultured cancer cell line, e.g., MCF-7 estrogen-receptor-positive human breast cancer cell line, is maintained in plastic tissue culture flasks (Costar) in DMEM with penicillin (100 ng/ml), streptomycin (100 $\mu$g/ml), 5% fetal calf serum, insulin (10 ng/ml), L-glutamine (2 mM) and non-essential amino acids (1%). Cells are seeded in 96-well V-bottomed plates (Linbro-Flow Laboratories, McLean, Va.) at a concentration of $1 \times 10^5$ per well in complete medium. Putative toxins are added to varying concentrations ($10^{-12}$M to $10^{-6}$M) and the cultures are incubated for 18 hrs. at 37° C. in a 5% $CO_2$ atmosphere. Following incubation, the plates are centrifuged for 5 min. at 170×g, and the medium removed and replaced with 100 $\mu$l leucine-free medium (MEM, Gibco) containing 8 $\mu$Ci/ml ($^3$H-leucine; New England Nuclear, Boston, Mass.). After an additional 90 min. at 37° C., the plates are centrifuged for 5 min. at 170×g, the medium is removed, and the cells are collected on glass fiber filters using a cell harvester (Skatron, Sterling, Va.). Filters are washed, dried, and counted according to standard methods. Cells cultured with medium alone serve as the control. A test compound which reduces or halts or inhibits cell growth compared to untreated control cells, is detected as an indication of toxicity and is considered useful in the invention.

Evaluation of whether a test compound confers protection against the development of a neoplasm (e.g., breast or prostate cancers) generally involves using an animal known to develop a neoplasm (e.g., the transgenic mouse described in U.S. Pat. No. 4,736,866). An appropriate animal is treated with the test compound according to standard methods, and a reduced incidence of neoplasm development, compared to untreated control animals, is detected as an indication of protection.

As is discussed below, I have discovered that unglycosylated rHuAFP produced in a prokaryotic expression system is effective in treating cancer. For example, rHuAFP has been found to be a potent inhibitor of breast carcinoma growth in vitro.

The experimental examples described below demonstrate the efficacy of rHuAFP as an anti-cancer agent. These examples are provided to illustrate, not limit, the invention.

Experimental

Materials and Methods

Culture Media and Tumor Cells

Dulbecco's modified Eagle's medium (DMEM), RPMI 1640, fetal calf serum, glutamine, non-essential amino acids and penicillin-streptomycin mixture were obtained from GIBCO (BRL). Donor calf serum was obtained from Hyclone, Logan, UT, and porcine insulin was obtained from Squibb, Inc., Princeton, N.J.

The MCF-7 estrogen-receptor-positive human breast cancer cell line was obtained from Dr. Alberto C. Baldi, Institute of Experimental Biology and Medicine, Buenos Aires, Argentina. Stock cultures were maintained in plastic tissue culture flasks (Costar) in DMEM with penicillin (100 U/ml), streptomycin (100 μg/ml), 5% fetal calf serum, insulin (10 ng/ml), L-glutamine (2 mM) and non-essential amino acids (1%).

Synthesis and Purification of rHuAFP

Recombinant HuAFP was synthesized and purified using the methods described in U.S. Pat. No. 5,384,250. rHuAFP can be obtained from Immtek, Inc. (Boston, Mass.).

Estrogen-Stimulated Post-confluent Growth of MCF-7 Cells in Culture

This assay is based on the finding that MCF-7 cells in estrogen-containing medium grow past confluence and accumulate into foci; but, in the absence of estrogen, cell proliferation stops after the cultures establish cell-cell contact, and no foci are formed (see, e.g., Gierthy et al., Breast Cancer Res. Treat. 12:227, 1988). $1 \times 10^7$ MCF-7 breast cancer cells were seeded in 16-mm wells contained in 24-well tissue culture plates. Culture medium was phenol red-free DMEM supplemented with 5% donor calf serum (prescreened for absence of detectable estrogens), L-glutamine (2 mM), non-essential amino acids (1×, GIBCO), insulin (10 ng/ml), penicillin-streptomycin (1×, GIBCO) and estradiol diluted to a final concentration of $1.8 \times 10^{-9}$ M. Cultures were refed at 24 hr and every 4 days thereafter with 2 ml of culture medium containing rHuAFP and human serum albumin to yield a final protein concentration of 100 μg/ml per well. Cells reached confluence within 5 days, and a substantial number of foci were apparent within 10 days in wells containing estrogen alone. Cells were fixed with buffered formalin and stained with 1% Rhodamine B. The stained foci were quantitated using an Artek 870 Macro-Micro Automated Colony Counter. Data are presented as mean number of foci per treatment group.

Results

Activity of rHuAFP Against MCF-7 Breast Cancer Cells

The results shown in FIG. 3 demonstrate that rHuAFP inhibits estrogen-stimulated postconfluent growth of MCF-7 breast cancer cells in vitro. Control experiments using human albumin or no protein had no effect on MCF-7 foci formation. These data indicate that rHuAFP has a direct inhibitory effect on the growth of carcinoma cell cultures.

Therapeutic Administration

As demonstrated above, rHuAFP is effective in inhibiting a neoplasm, e.g., a breast cell carcinoma. Accordingly, compounds of the invention can be formulated according to known methods to prepare pharmaceutically useful compositions. Treatment of human patients will be carried out using a therapeutically effective amount of an anti-cancer agent of rHuAFP in a physiologically acceptable carrier. Suitable carriers and their formulation are described for example in Remington's *Pharmaceutical Sciences* by E. W. Martin. The amount of the anti-cancer agent to be administered varies depending upon the manner of administration, the age and body weight of the patient, and with the type of disease, extensiveness of the disease, and size of the patient suffering from the disease. Generally amounts will be in the range of those used for other agents used in the treatment of cancer, although in certain instances lower amounts will be needed because of the increased specificity of the compound. For example, rHuAFP is administered systemically, as described below, at a dosage that inhibits malignant cell proliferation, typically in the range of 0.1 ng–10 g/kg body weight.

Furthermore, the method of the invention can also employ combination therapy in which rHuAFP is administered either simultaneously or sequentially with a chemotherapeutic agent. Typically, a chemotherapeutic agent is administered according to standard methods or, alternatively, in a dose which is lower than the standard dose when the chemotherapeutic agent is used by itself. Examples of chemotherapeutic agents include, without limitation, mechlorethamine, cyclophosphamide, ifosfamide, L-sarcolysin, chlorambucil, hexamethylmelamine, thiotepa, busulfan, carmustine, lomustine, semustine, streptozocin, dacarbazine, methotrexate, fluorouracil, cytarabine, mercaptopurine, thibguanine, pentostatin, vinblastine, vincristine, etoposide, teniposide, actinomycin D, daunomycin, doxorubicin, bleomycin, plicamycin, mitomycin, cisplatin, mitoxantrone, hydroxyurea, procarbozine, mitotane, aminoglutethimide, prednisone, hydroxyprogesterone, diethylstilbestrol, tamoxifen, flutamide, or leuprolide.

Treatment is started generally with the diagnosis or suspicion of a neoplasm and is generally repeated on a daily basis. Protection from the development of neoplasm is also achieved by administration of rHuAFP on a daily basis. If desired, the efficacy of the treatment or protection regimens is assessed with the methods of monitoring or diagnosing patients for cancer.

Furthermore, the compounds of the invention can also be used to treat mammals to destroy any unwanted cells bearing alpha-fetoprotein receptors associated with a pathological condition. The method(s) of the invention can also be used to treat non-human mammals, for example, domestic pets, or livestock. As described below, the anti-cancer agents of the invention can be administered systemically or locally.

Systemic Administration

For use as an anti-cancer agent, the compounds of the invention can be administered systemically, for example, formulated in a pharmaceutically-acceptable buffer such as physiological saline. Preferable routes of administration include, for example, subcutaneous, intravenous, interperitoneally, intramuscular, or intradermal injections which provide continuous, sustained levels of the drug in the patient. In other preferred routes of administration, the compounds of the invention can be given to a patient by injection of a slow release preparation, for example, in a slowly dissociating polymeric or crystalline form; this sort of sustained administration can follow an initial delivery of the drug by more conventional routes (for example, those described above). Alternatively, the compounds can be administered using an infusion pump, thus allowing a precise degree of control over the rate of drug release, or through installation of the compounds in the nasal passages in a similar fashion to that used to promote absorption of insulin. As an alternative to nasal transmucosal absorption, the compounds can be delivered by aerosol deposition of the powder or solution into the lungs.

Local Administration

The anti-cancer agents of the invention also can be administered locally to treat cancer. Since the desired action of the agent is generally upon a circumscribed mass of tissue, for example a tumor, delivery of the drug by means which result in high local concentrations in the vicinity of the tumor is especially desirable.

Recombinant HuAFP as a Diagnostic Agent

Recombinant HuAFP (or fragment or analog thereof) linked to a detectable label finds diagnostic use in the detection or monitoring or assaying for the presence of a neoplasm (e.g., breast or prostate cancers).

For example, in vivo studies can be conducted on human patients to determine the presence of a neoplasm using a detectably labelled rHuAFP (e.g., Tc-99m-labelled rHuAFP). In general, the detectably labelled rHuAFP is administered intravenously and imaging can be performed using scanners by methods known to those skilled in the art, e.g., by radioimaging using scintigraphy.

In another working example, a neoplasm or any cell bearing a receptor which is recognized by rHuAFP may be detected in a tissue sample, e.g., a biopsy, a bodily fluid, by using rHuAFP (or fragment or analog thereof) linked to a detectable label. After determining that a patient should be tested for the presence of such cells, a tissue sample, a biopsy, or a sample of bodily fluid, preferably lymph, blood, serum, or urine, is collected from the patient. Accordingly, the subcellular location or presence of a receptor which is recognized by rHuAFP is determined either in situ or in vitro using fractionated cells by any standard biochemical or histochemical procedure (see e.g., Ausubel et al., supra; Bancroft and Stevens, *Theory and Practice of Histological Techniques*, Churchill Livingstone, 1982). Appropriate control samples for the assay include a tissue sample or a bodily fluid collected from individuals who do not have cells bearing alpha-fetoprotein (negative control), or samples which contain a known, predetermined amount of alpha-fetoprotein receptor (positive control).

The diagnostic assay may be performed in solution or may use a solid (insoluble) support (e.g. polystyrene, nitrocellulose, or beads) or in a tissue sample prepared for histological examination, using any standard methods. For example, to determine whether the patient from whom the test sample was collected has cells bearing receptors which is recognized by rHuAFP, the level of binding of the detectably labelled rHuAFP in the test sample is compared to the level of binding in the negative and/or positive control samples. A level of binding in the test sample greater than the level of binding in the negative control sample, or at least equal to the level of binding in the positive control sample, indicates that the patient has cells bearing alpha-fetoprotein receptors.

Materials for performing the diagnostic assays according to the methods of the invention may be provided as a kit having instructions for use. In general, the kit is composed in part of a rHuAFP (or fragment or analog thereof). This kit may further include a second reagent, e.g., a detectable label, which is used to label rHuAFP (or a fragment or analog thereof). The kits exemplified above are useful in, for example, detecting the presence of a tumor in a sample of human tissue in vitro, or for in vivo examination purposes.

The experimental examples described below demonstrate the efficacy of rHuAFP diagnosing a neoplasm. These examples are provided to illustrate, not limit, the invention.

Experimental

Materials and Methods

Animals

MCF-7 human breast cancer cells implanted in the lateral thorax region of CB-17 SCID mice were grown to a size of 1 cm diameter (approx. 5 gm) under estrogen stimulation according to methods known in the art.

Technetium Labelling

99mTc-recombinant labelled alpha-fetoprotein was prepared from an AFP aliquot mixed with 0.5 ml 0.9% sodium chloride injection solution (Baxter Healthcare Corporation, Deerfield, Ill.). The solution is added to an UltraTag RBC Reaction Vial (Mallinckrodt Medical Inc., St. Louis, Mo. 63134 Lot No. 0683040), containing stannous chloride dihydrate, sodium citrate dihydrate, and dextrose anhydrous, in a lyophilized form stored under argon. The contents of the vial are mixed by gentle swirling, and incubated at room temperature for 5 minutes. At the completion of the incubation, 0.8–1.2 Gbq Technetium 99mTc Sodium Pertechnetate Injection is added (99mTc Generator Mallincrokt Medical, Inc. St. Louis, Mo.) in a volume of 1–2 ml. The contents of the vial are mixed by gentle swirling and incubated for 15 minutes. Dose aliquots were assayed at 0, 3, and 6 hours after preparation. Thin-layer chromatography performed on preparations using ITLC-SG (Gelman Instrument Co., Ann Arbor, Mich.) with 0.9% NaCl showed 95–99% of the 99Tc was bound to the recombinant alpha-fetoprotein.

Imaging

Experimental animals are sedated with Medafane. A 24 gauge, ¾ inch catheter (Surflo IV catheter, Terumo Medical) is then secured in a lateral tail vein. The animal is then further anesthetized with a slow infusion of 20–25 mg/kg body weight of pentobarbital intravenously. Anesthesia is maintained for restraint as required with injections of 5 mg of additional pentobarbital.

Isotope biodistribution data is collected using a Elscint Dymax 409 gamma camera. This data is subsequently analyzed by a computer (Siemans Gammasonics Microdelta). Animals are imaged in triples, being placed in the dorsal recumbent position on a thin polyethylene panel. To eliminate motion during imaging, the animals are restrained as necessary, on these panels by strips of tape over their extremities so as not to restrict respiration. Dynamic images obtained over 60 minutes are used to determine the biodistribution of the labeled protein. Typically, twelve sequential, five minute images are obtained with low energy general purpose collimation, and 1.5 hardware zoom into the computer matrices having 128 by 128 picture elements. Study animals are typically injected with 37MBq of Tc-99m labelled protein.

Results

Tracer Biodistribution and Kinetics

Following administration of 37MBq (approx. 4–6 µg Tc-99m recombinant human alpha-fetoprotein) in the tail vein, tracer biodistribution kinetics were measured during the initial hour after injection and at 24 hours. Tissue uptake kinetics were measured in % injected activity/per 100 ROI (Region of Interest) pixels (%IA). During the first hour there is rapid renal clearance, mild localization in the liver and little evident activity in other tissues. At 1 hour, tumor uptake was (mean±SEM: 1.9±0.3%IA) and the tumor to heart (T/H) region ratio was 0.84±0.23. By 24 hours, tumor uptake was (0.8+/−0.1%IA) and T/A and tumor to background (T/B upper chest) region ratios were 1.43±0.41 and 2.66±0.54, respectively. Studies comparing 99mTc-labelled rHuAFP to 99mTc-labelled human serum albumin (used as a non-specific protein control) repeated in the same animals showed that T/B image ROI activity ration was 2.7 and 5.8 for 99mTc-labelled rHuAFP at 1 and 24 hr, respectively and at 24 hours was 40% greater for 99mTc-labelled rHuAFP compared to Tc-99m human serum albumin. These results show that rHuAFP can be labelled with Tc-99m and that this labelled agent has low non-specific tissue uptake and rapid renal clearance from the blood. Localization in human breast cancer xenografts is initially rapid, increases with time, and is due to specific tumor uptake. These results demonstrate that rHuAFP labelled with Tc-99m is useful as a diagnostic agent for breast carcinoma.

Diagnostic Administration

As discussed above, rHuAFP (or fragment or analog thereof) linked to a detectable label finds diagnostic use in the detection or monitoring or assaying of a neoplasm (e.g., a breast cell carcinoma). Accordingly, patients who present with the classical symptoms of cancer, e.g., breast cancer or prostate cancer, or have a medical history which indicates susceptibility to such cancer may be tested with the methods of the invention. Other appropriate patients for such testing include those who have a family history of breast or prostate carcinomas. Patients who are receiving drugs or have been exposed to toxins implicated in the induction of a cancer should also be tested.

The diagnostic methods employing detectably labelled rHuAFP (or a fragment or analog thereof) of the invention may be used to detect the presence of a cancer prior to, or after the onset of, clinical symptoms associated with the cancer.

The method of the invention facilitates diagnosis of a neoplasm prior to or coincident with the onset of clinical symptoms (e.g., a palpable tumorous mass). For example, the method of the subject invention may provide a diagnosis of breast cancer prior to onset of clinical symptoms. Furthermore, the method of the invention allows the clinician to provide an accurate diagnosis of a neoplasm such as breast or prostate cancer.

Diagnostic imaging methods of the invention will be carried out using a diagnostically effective amount of a diagnostic agent of rHuAFP in a physiologically acceptable carrier. Suitable carriers and their formulation are described for example in Remington's *Pharmaceutical Sciences* by E. W. Martin. The amount of the diagnostic agent to be administered varies depending upon the manner of administration, the age and body weight of the patient, and with the type of disease, extensiveness of the disease, and size of the patient suffering from the disease. Generally, however, amounts will be in the range of those used for other agents used in the diagnosis of cancer, although in certain instances lower amounts will be needed because of the increased specificity of the compound. For example, a detectably labelled rHuAFP is administered intravenously to a patient, as is described above, at a dosage that allows imaging of a neoplasm, e.g., by radioimaging using scintigraphy. Typically, a dosage is in the range of 0.1 ng–10 g/kg body weight.

All publications, patents, and patent applications mentioned in this specification are herein incorporated by reference to the same extent as if each individual publication or patent application was specifically and individually indicated to be incorporated by reference.

What is claimed is:

1. A hybrid cytotoxin consisting essentially of a recombinant human alpha-fetoprotein (SEQ ID NO:2) or a fragment thereof selected from the group comprsing at least one of Domain I (SEQ ID NO:3), Domain II (SEQ ID NO:4), Domain III (SEQ ID NO:5), Domain I+II (SEQ ID NO:6), Domain II+III (SEQ ID NO:7), and rHuAFP Fragment I (SEQ ID NO:8) linked to a cytotoxic agent.

2. The hybrid cytotoxin of claim 1, wherein said cytotoxic agent is a protein.

3. The hybrid cytotoxin of claim 1, wherein said cytotoxic agent is chemically conjugated to said recombinant human alpha-fetoprotein or fragment thereof.

4. The hybrid cytotoxin of claim 1, wherein said cytotoxin is linked by a peptide bond to said recombinant human alpha-fetoprotein or fragment thereof, and said hybrid toxin is produced by expression of a genetically engineered hybrid DNA molecule.

* * * * *

SEQUENCE LISTING

<160> NUMBER OF SEQ ID NOS: 16

<210> SEQ ID NO 1
<211> LENGTH: 2022
<212> TYPE: DNA
<213> ORGANISM: Homo sapiens

<400> SEQUENCE: 1

```
atattgtgct tccaccactg ccaataacaa aataactagc aaccatgaag tgggtggaat      60
caattttttt aattttccta ctaaattta ctgaatccag aacactgcat agaaatgaat     120
atggaatagc ttccatattg gattcttacc aatgtactgc agagataagt ttagctgacc     180
tggctaccat attttttgcc cagtttgttc aagaagccac ttacaaggaa gtaagcaaaa     240
tggtgaaaga tgcattgact gcaattgaga aacccactgg agatgaacag tcttcagggt     300
gtttagaaaa ccagctacct gcctttctgg aagaactttg ccatgagaaa gaaattttgg     360
agaagtacgg acattcagac tgctgcagcc aaagtgaaga gggaagacat aactgttttc     420
ttgcacacaa aaagcccact gcagcatgga tcccactttt ccaagttcca gaacctgtca     480
caagctgtga agcatatgaa gaagacaggg agacattcat gaacaaattc atttatgaga     540
tagcaagaag gcatccttc ctgtatgcac ctacaattct tctttcggct gctgggtatg      600
agaaaataat tccatcttgc tgcaaagctg aaaatgcagt tgaatgcttc caaacaaagg     660
cagcaacagt tacaaaagaa ttaagagaaa gcagcttgtt aaatcaacat gcatgtccag     720
taatgaaaaa ttttgggacc cgaactttcc aagccataac tgttactaaa ctgagtcaga     780
```

```
agtttaccaa agttaatttt actgaaatcc agaaactagt cctggatgtg gcccatgtac    840
atgagcactg ttgcagagca gatgtgctgg attgtctgca ggatggggaa aaaatcatgt    900
cctacatatg ttctcaacaa gacactctgt caaacaaaat aacagaatgc tgcaaactga    960
ccacgctgga acgtggtcaa tgtataattc atgcagaaaa tgatgaaaaa cctgaaggtc   1020
tatctccaaa tctaaacagg ttttaggag atagagattt taaccaattt tcttcagggg    1080
aaaaaaatat cttcttggca agttttgttc atgaatattc aagaagacat cctcagcttg   1140
ctgtctcagt aattctaaga gttgctaaag gataccagga gttattggag aagtgtttcc   1200
agactgaaaa ccctcttgaa tgccaagata aggagaaga agaattacag aaatacatcc    1260
aggagagcca agcattggca aagcgaagct gcggcctctt ccagaaacta ggagaatatt   1320
acttacaaaa tgagtttctc gttgcttaca caaagaaagc cccccagctg acctcgtcgg   1380
agctgatggc catcaccaga aaatggcag ccacagcagc cacttgttgc caactcagtg    1440
aggacaaact attggcctgt ggcgagggag cggctgacat tattatcgga cacttatgta   1500
tcagacatga atgactcca gtaaaccctg tgttggcca gtgctgcact tcttcatatg     1560
ccaacaggag gccatgcttc agcagcttgg tggtggatga acatatgtc cctcctgcat    1620
tctctgatga caagttcatt ttccataagg atctgtgcca agctcagggt gtagcgctgc   1680
aaaggatgaa gcaagagttt ctcattaacc ttgtgaagca aaagccacaa ataacagagg   1740
aacaacttga ggctctcatt gcagatttct caggcctgtt ggagaaatgc tgccaaggcc   1800
aggaacagga agtctgcttt gctgaagagg gacaaaaact gatttcaaaa actggtgctg   1860
ctttgggagt ttaaattact tcaggggaag agaagacaaa acgagtcttt cattcggtgt   1920
gaacttttct ctttaatttt aactgattta acactttttg tgaattaatg ataaagactt   1980
ttatgtgaga tttccttatc acagaaataa aatatctcca aa                     2022

<210> SEQ ID NO 2
<211> LENGTH: 590
<212> TYPE: PRT
<213> ORGANISM: Homo sapiens

<400> SEQUENCE: 2

Thr Leu His Arg Asn Glu Tyr Gly Ile Ala Ser Ile Leu Asp Ser Tyr
 1               5                  10                  15

Gln Cys Thr Ala Glu Ile Ser Leu Ala Asp Leu Ala Thr Ile Phe Phe
            20                  25                  30

Ala Gln Phe Val Gln Glu Ala Thr Tyr Lys Glu Val Ser Lys Met Val
        35                  40                  45

Lys Asp Ala Leu Thr Ala Ile Glu Lys Pro Thr Gly Asp Glu Gln Ser
    50                  55                  60

Ser Gly Cys Leu Glu Asn Gln Leu Pro Ala Phe Leu Glu Glu Leu Cys
65                  70                  75                  80

His Glu Lys Glu Ile Leu Glu Lys Tyr Gly His Ser Asp Cys Cys Ser
                85                  90                  95

Gln Ser Glu Glu Gly Arg His Asn Cys Phe Leu Ala His Lys Lys Pro
            100                 105                 110

Thr Ala Ala Trp Ile Pro Leu Phe Gln Val Pro Glu Pro Val Thr Ser
        115                 120                 125

Cys Glu Ala Tyr Glu Glu Asp Arg Glu Thr Phe Met Asn Lys Phe Ile
    130                 135                 140

Tyr Glu Ile Ala Arg Arg His Pro Phe Leu Tyr Ala Pro Thr Ile Leu
145                 150                 155                 160
```

-continued

Leu Ser Ala Ala Gly Tyr Glu Lys Ile Ile Pro Ser Cys Cys Lys Ala
                165                 170                 175
Glu Asn Ala Val Glu Cys Phe Gln Thr Lys Ala Ala Thr Val Thr Lys
            180                 185                 190
Glu Leu Arg Glu Ser Ser Leu Leu Asn Gln His Ala Cys Pro Val Met
        195                 200                 205
Lys Asn Phe Gly Thr Arg Thr Phe Gln Ala Ile Thr Val Thr Lys Leu
    210                 215                 220
Ser Gln Lys Phe Thr Lys Val Asn Phe Thr Glu Ile Gln Lys Leu Val
225                 230                 235                 240
Leu Asp Val Ala His Val His Glu His Cys Cys Arg Ala Asp Val Leu
            245                 250                 255
Asp Cys Leu Gln Asp Gly Glu Lys Ile Met Ser Tyr Ile Cys Ser Gln
        260                 265                 270
Gln Asp Thr Leu Ser Asn Lys Ile Thr Glu Cys Cys Lys Leu Thr Thr
    275                 280                 285
Leu Glu Arg Gly Gln Cys Ile Ile His Ala Glu Asn Asp Glu Lys Pro
290                 295                 300
Glu Gly Leu Ser Pro Asn Leu Asn Arg Phe Leu Gly Asp Arg Asp Phe
305                 310                 315                 320
Asn Gln Phe Ser Ser Gly Glu Lys Asn Ile Phe Leu Ala Ser Phe Val
            325                 330                 335
His Glu Tyr Ser Arg Arg His Pro Gln Leu Ala Val Ser Val Ile Leu
        340                 345                 350
Arg Val Ala Lys Gly Tyr Gln Glu Leu Leu Glu Lys Cys Phe Gln Thr
    355                 360                 365
Glu Asn Pro Leu Glu Cys Gln Asp Lys Gly Glu Glu Glu Leu Gln Lys
    370                 375                 380
Tyr Ile Gln Glu Ser Gln Ala Leu Ala Lys Arg Ser Cys Gly Leu Phe
385                 390                 395                 400
Gln Lys Leu Gly Glu Tyr Tyr Leu Gln Asn Glu Phe Leu Val Ala Tyr
            405                 410                 415
Thr Lys Lys Ala Pro Gln Leu Thr Ser Ser Glu Leu Met Ala Ile Thr
        420                 425                 430
Arg Lys Met Ala Ala Thr Ala Ala Thr Cys Cys Gln Leu Ser Glu Asp
    435                 440                 445
Lys Leu Leu Ala Cys Gly Glu Gly Ala Ala Asp Ile Ile Ile Gly His
450                 455                 460
Leu Cys Ile Arg His Glu Met Thr Pro Val Asn Pro Gly Val Gly Gln
465                 470                 475                 480
Cys Cys Thr Ser Ser Tyr Ala Asn Arg Arg Pro Cys Phe Ser Ser Leu
            485                 490                 495
Val Val Asp Glu Thr Tyr Val Pro Pro Ala Phe Ser Asp Asp Lys Phe
        500                 505                 510
Ile Phe His Lys Asp Leu Cys Gln Ala Gln Gly Val Ala Leu Gln Arg
    515                 520                 525
Met Lys Gln Glu Phe Leu Ile Asn Leu Val Lys Gln Lys Pro Gln Ile
    530                 535                 540
Thr Glu Glu Gln Leu Glu Ala Leu Ile Ala Asp Phe Ser Gly Leu Leu
545                 550                 555                 560
Glu Lys Cys Cys Gln Gly Gln Glu Gln Glu Val Cys Phe Ala Glu Glu
            565                 570                 575

```
Gly Gln Lys Leu Ile Ser Lys Thr Gly Ala Ala Leu Gly Val
            580                 585                 590

<210> SEQ ID NO 3
<211> LENGTH: 197
<212> TYPE: PRT
<213> ORGANISM: Homo sapiens

<400> SEQUENCE: 3

Thr Leu His Arg Asn Glu Tyr Gly Ile Ala Ser Ile Leu Asp Ser Tyr
  1               5                  10                  15

Gln Cys Thr Ala Glu Ile Ser Leu Ala Asp Leu Ala Thr Ile Phe Phe
                 20                  25                  30

Ala Gln Phe Val Gln Glu Ala Thr Tyr Lys Glu Val Ser Lys Met Val
             35                  40                  45

Lys Asp Ala Leu Thr Ala Ile Glu Lys Pro Thr Gly Asp Glu Gln Ser
 50                  55                  60

Ser Gly Cys Leu Glu Asn Gln Leu Pro Ala Phe Leu Glu Glu Leu Cys
 65                  70                  75                  80

His Glu Lys Glu Ile Leu Glu Lys Tyr Gly His Ser Asp Cys Cys Ser
                 85                  90                  95

Gln Ser Glu Glu Gly Arg His Asn Cys Phe Leu Ala His Lys Lys Pro
            100                 105                 110

Thr Ala Ala Trp Ile Pro Leu Phe Gln Val Pro Glu Pro Val Thr Ser
        115                 120                 125

Cys Glu Ala Tyr Glu Glu Asp Arg Glu Thr Phe Met Asn Lys Phe Ile
130                 135                 140

Tyr Glu Ile Ala Arg Arg His Pro Phe Leu Tyr Ala Pro Thr Ile Leu
145                 150                 155                 160

Leu Ser Ala Ala Gly Tyr Glu Lys Ile Ile Pro Ser Cys Cys Lys Ala
                165                 170                 175

Glu Asn Ala Val Glu Cys Phe Gln Thr Lys Ala Ala Thr Val Thr Lys
            180                 185                 190

Glu Leu Arg Glu Ser
            195

<210> SEQ ID NO 4
<211> LENGTH: 192
<212> TYPE: PRT
<213> ORGANISM: Homo sapiens

<400> SEQUENCE: 4

Ser Leu Leu Asn Gln His Ala Cys Pro Val Met Lys Asn Phe Gly Thr
  1               5                  10                  15

Arg Thr Phe Gln Ala Ile Thr Val Thr Lys Leu Ser Gln Lys Phe Thr
                 20                  25                  30

Lys Val Asn Phe Thr Glu Ile Gln Lys Leu Val Leu Asp Val Ala His
             35                  40                  45

Val His Glu His Cys Cys Arg Ala Asp Val Leu Asp Cys Leu Gln Asp
 50                  55                  60

Gly Glu Lys Ile Met Ser Tyr Ile Cys Ser Gln Gln Asp Thr Leu Ser
 65                  70                  75                  80

Asn Lys Ile Thr Glu Cys Cys Lys Leu Thr Thr Leu Glu Arg Gly Gln
                 85                  90                  95

Cys Ile Ile His Ala Glu Asn Asp Glu Lys Pro Glu Gly Leu Ser Pro
            100                 105                 110
```

-continued

Asn Leu Asn Arg Phe Leu Gly Asp Arg Asp Phe Asn Gln Phe Ser Ser
            115                 120                 125

Gly Glu Lys Asn Ile Phe Leu Ala Ser Phe Val His Glu Tyr Ser Arg
        130                 135                 140

Arg His Pro Gln Leu Ala Val Ser Val Ile Leu Arg Val Ala Lys Gly
145                 150                 155                 160

Tyr Gln Glu Leu Leu Glu Lys Cys Phe Gln Thr Glu Asn Pro Leu Glu
                165                 170                 175

Cys Gln Asp Lys Gly Glu Glu Glu Leu Gln Lys Tyr Ile Gln Glu Ser
            180                 185                 190

<210> SEQ ID NO 5
<211> LENGTH: 201
<212> TYPE: PRT
<213> ORGANISM: Homo sapiens

<400> SEQUENCE: 5

Gln Ala Leu Ala Lys Arg Ser Cys Gly Leu Phe Gln Lys Leu Gly Glu
1               5                   10                  15

Tyr Tyr Leu Gln Asn Glu Phe Leu Val Ala Tyr Thr Lys Lys Ala Pro
            20                  25                  30

Gln Leu Thr Ser Ser Glu Leu Met Ala Ile Thr Arg Lys Met Ala Ala
        35                  40                  45

Thr Ala Ala Thr Cys Cys Gln Leu Ser Glu Asp Lys Leu Leu Ala Cys
    50                  55                  60

Gly Glu Gly Ala Ala Asp Ile Ile Gly His Leu Cys Ile Arg His
65                  70                  75                  80

Glu Met Thr Pro Val Asn Pro Gly Val Gly Gln Cys Cys Thr Ser Ser
                85                  90                  95

Tyr Ala Asn Arg Arg Pro Cys Phe Ser Ser Leu Val Val Asp Glu Thr
            100                 105                 110

Tyr Val Pro Pro Ala Phe Ser Asp Asp Lys Phe Ile Phe His Lys Asp
        115                 120                 125

Leu Cys Gln Ala Gln Gly Val Ala Leu Gln Arg Met Lys Gln Glu Phe
    130                 135                 140

Leu Ile Asn Leu Val Lys Gln Lys Pro Gln Ile Thr Glu Glu Gln Leu
145                 150                 155                 160

Glu Ala Leu Ile Ala Asp Phe Ser Gly Leu Leu Glu Lys Cys Cys Gln
                165                 170                 175

Gly Gln Glu Gln Glu Val Cys Phe Ala Glu Gly Gln Lys Leu Ile
            180                 185                 190

Ser Lys Thr Gly Ala Ala Leu Gly Val
        195                 200

<210> SEQ ID NO 6
<211> LENGTH: 389
<212> TYPE: PRT
<213> ORGANISM: Homo sapiens

<400> SEQUENCE: 6

Thr Leu His Arg Asn Glu Tyr Gly Ile Ala Ser Ile Leu Asp Ser Tyr
1               5                   10                  15

Gln Cys Thr Ala Glu Ile Ser Leu Ala Asp Leu Ala Thr Ile Phe Phe
            20                  25                  30

Ala Gln Phe Val Gln Glu Ala Thr Tyr Lys Glu Val Ser Lys Met Val
        35                  40                  45

```
Lys Asp Ala Leu Thr Ala Ile Glu Lys Pro Thr Gly Asp Glu Gln Ser
     50                  55                  60

Ser Gly Cys Leu Glu Asn Gln Leu Pro Ala Phe Leu Glu Glu Leu Cys
 65                  70                  75                  80

His Glu Lys Glu Ile Leu Glu Lys Tyr Gly His Ser Asp Cys Cys Ser
                 85                  90                  95

Gln Ser Glu Glu Gly Arg His Asn Cys Phe Leu Ala His Lys Lys Pro
            100                 105                 110

Thr Ala Ala Trp Ile Pro Leu Phe Gln Val Pro Glu Pro Val Thr Ser
            115                 120                 125

Cys Glu Ala Tyr Glu Glu Asp Arg Glu Thr Phe Met Asn Lys Phe Ile
            130                 135                 140

Tyr Glu Ile Ala Arg Arg His Pro Phe Leu Tyr Ala Pro Thr Ile Leu
145                 150                 155                 160

Leu Ser Ala Ala Gly Tyr Glu Lys Ile Ile Pro Ser Cys Cys Lys Ala
                165                 170                 175

Glu Asn Ala Val Glu Cys Phe Gln Thr Lys Ala Ala Thr Val Thr Lys
            180                 185                 190

Glu Leu Arg Glu Ser Ser Leu Leu Asn Gln His Ala Cys Pro Val Met
            195                 200                 205

Lys Asn Phe Gly Thr Arg Thr Phe Gln Ala Ile Thr Val Thr Lys Leu
210                 215                 220

Ser Gln Lys Phe Thr Lys Val Asn Phe Thr Glu Ile Gln Lys Leu Val
225                 230                 235                 240

Leu Asp Val Ala His Val His Glu His Cys Cys Arg Ala Asp Val Leu
                245                 250                 255

Asp Cys Leu Gln Asp Gly Glu Lys Ile Met Ser Tyr Ile Cys Ser Gln
            260                 265                 270

Gln Asp Thr Leu Ser Asn Lys Ile Thr Glu Cys Cys Lys Leu Thr Thr
            275                 280                 285

Leu Glu Arg Gly Gln Cys Ile Ile His Ala Glu Asn Asp Glu Lys Pro
            290                 295                 300

Glu Gly Leu Ser Pro Asn Leu Asn Arg Phe Leu Gly Asp Arg Asp Phe
305                 310                 315                 320

Asn Gln Phe Ser Ser Gly Glu Lys Asn Ile Phe Leu Ala Ser Phe Val
                325                 330                 335

His Glu Tyr Ser Arg Arg His Pro Gln Leu Ala Val Ser Val Ile Leu
            340                 345                 350

Arg Val Ala Lys Gly Tyr Gln Glu Leu Leu Glu Lys Cys Phe Gln Thr
            355                 360                 365

Glu Asn Pro Leu Glu Cys Gln Asp Lys Gly Glu Glu Leu Gln Lys
            370                 375                 380

Tyr Ile Gln Glu Ser
385

<210> SEQ ID NO 7
<211> LENGTH: 393
<212> TYPE: PRT
<213> ORGANISM: Homo sapiens

<400> SEQUENCE: 7

Ser Leu Leu Asn Gln His Ala Cys Pro Val Met Lys Asn Phe Gly Thr
 1               5                  10                  15

Arg Thr Phe Gln Ala Ile Thr Val Thr Lys Leu Ser Gln Lys Phe Thr
             20                  25                  30
```

Lys Val Asn Phe Thr Glu Ile Gln Lys Leu Val Leu Asp Val Ala His
            35                  40                  45

Val His Glu His Cys Cys Arg Ala Asp Val Leu Asp Cys Leu Gln Asp
    50                  55                  60

Gly Glu Lys Ile Met Ser Tyr Ile Cys Ser Gln Gln Asp Thr Leu Ser
65                  70                  75                  80

Asn Lys Ile Thr Glu Cys Cys Lys Leu Thr Thr Leu Glu Arg Gly Gln
                85                  90                  95

Cys Ile Ile His Ala Glu Asn Asp Glu Lys Pro Glu Gly Leu Ser Pro
                100                 105                 110

Asn Leu Asn Arg Phe Leu Gly Asp Arg Asp Phe Asn Gln Phe Ser Ser
            115                 120                 125

Gly Glu Lys Asn Ile Phe Leu Ala Ser Phe Val His Glu Tyr Ser Arg
        130                 135                 140

Arg His Pro Gln Leu Ala Val Ser Val Ile Leu Arg Val Ala Lys Gly
145                 150                 155                 160

Tyr Gln Glu Leu Leu Glu Lys Cys Phe Gln Thr Glu Asn Pro Leu Glu
                165                 170                 175

Cys Gln Asp Lys Gly Glu Glu Glu Leu Gln Lys Tyr Ile Gln Glu Ser
                180                 185                 190

Gln Ala Leu Ala Lys Arg Ser Cys Gly Leu Phe Gln Lys Leu Gly Glu
            195                 200                 205

Tyr Tyr Leu Gln Asn Glu Phe Leu Val Ala Tyr Thr Lys Lys Ala Pro
        210                 215                 220

Gln Leu Thr Ser Ser Glu Leu Met Ala Ile Thr Arg Lys Met Ala Ala
225                 230                 235                 240

Thr Ala Ala Thr Cys Cys Gln Leu Ser Glu Asp Lys Leu Leu Ala Cys
                245                 250                 255

Gly Glu Gly Ala Ala Asp Ile Ile Ile Gly His Leu Cys Ile Arg His
                260                 265                 270

Glu Met Thr Pro Val Asn Pro Gly Val Gly Gln Cys Cys Thr Ser Ser
            275                 280                 285

Tyr Ala Asn Arg Arg Pro Cys Phe Ser Ser Leu Val Val Asp Glu Thr
        290                 295                 300

Tyr Val Pro Pro Ala Phe Ser Asp Asp Lys Phe Ile Phe His Lys Asp
305                 310                 315                 320

Leu Cys Gln Ala Gln Gly Val Ala Leu Gln Arg Met Lys Gln Glu Phe
                325                 330                 335

Leu Ile Asn Leu Val Lys Gln Lys Pro Gln Ile Thr Glu Glu Gln Leu
            340                 345                 350

Glu Ala Leu Ile Ala Asp Phe Ser Gly Leu Leu Glu Lys Cys Cys Gln
        355                 360                 365

Gly Gln Glu Gln Glu Val Cys Phe Ala Glu Glu Gly Lys Leu Ile
    370                 375                 380

Ser Lys Thr Gly Ala Ala Leu Gly Val
385                 390

<210> SEQ ID NO 8
<211> LENGTH: 325
<212> TYPE: PRT
<213> ORGANISM: Homo sapiens

<400> SEQUENCE: 8

Met Ser Tyr Ile Cys Ser Gln Gln Asp Thr Leu Ser Asn Lys Ile Thr

-continued

```
  1               5               10              15
Glu Cys Cys Lys Leu Thr Thr Leu Glu Arg Gly Gln Cys Ile Ile His
             20              25              30

Ala Glu Asn Asp Glu Lys Pro Glu Gly Leu Ser Pro Asn Leu Asn Arg
             35              40              45

Phe Leu Gly Asp Arg Asp Phe Asn Gln Phe Ser Gly Glu Lys Asn
 50              55              60

Ile Phe Leu Ala Ser Phe Val His Glu Tyr Ser Arg Arg His Pro Gln
 65              70              75              80

Leu Ala Val Ser Val Ile Leu Arg Val Ala Lys Gly Tyr Gln Glu Leu
             85              90              95

Leu Glu Lys Cys Phe Gln Thr Glu Asn Pro Leu Glu Cys Gln Asp Lys
             100             105             110

Gly Glu Glu Glu Leu Gln Lys Tyr Ile Gln Glu Ser Gln Ala Leu Ala
             115             120             125

Lys Arg Ser Cys Gly Leu Phe Gln Lys Leu Gly Glu Tyr Tyr Leu Gln
 130             135             140

Asn Glu Phe Leu Val Ala Tyr Thr Lys Lys Ala Pro Gln Leu Thr Ser
145             150             155             160

Ser Glu Leu Met Ala Ile Thr Arg Lys Met Ala Ala Thr Ala Ala Thr
             165             170             175

Cys Cys Gln Leu Ser Glu Asp Lys Leu Leu Ala Cys Gly Glu Gly Ala
             180             185             190

Ala Asp Ile Ile Ile Gly His Leu Cys Ile Arg His Glu Met Thr Pro
             195             200             205

Val Asn Pro Gly Val Gly Gln Cys Cys Thr Ser Ser Tyr Ala Asn Arg
             210             215             220

Arg Pro Cys Phe Ser Ser Leu Val Val Asp Glu Thr Tyr Val Pro Pro
225             230             235             240

Ala Phe Ser Asp Asp Lys Phe Ile Phe His Lys Asp Leu Cys Gln Ala
             245             250             255

Gln Gly Val Ala Leu Gln Arg Met Lys Gln Glu Phe Leu Ile Asn Leu
             260             265             270

Val Lys Gln Lys Pro Gln Ile Thr Glu Glu Gln Leu Glu Ala Leu Ile
             275             280             285

Ala Asp Phe Ser Gly Leu Leu Glu Lys Cys Cys Gln Gly Gln Glu Gln
             290             295             300

Glu Val Cys Phe Ala Glu Glu Gly Gln Lys Leu Ile Ser Lys Thr Gly
305             310             315             320

Ala Ala Leu Gly Val
             325

<210> SEQ ID NO 9
<211> LENGTH: 30
<212> TYPE: DNA
<213> ORGANISM: Homo sapiens

<400> SEQUENCE: 9
aaaaaaggta ccacactgca tagaaatgaa                                    30

<210> SEQ ID NO 10
<211> LENGTH: 33
<212> TYPE: DNA
<213> ORGANISM: Homo sapiens

<400> SEQUENCE: 10
```

-continued

```
aaaaaaggat ccttagcttt ctcttaattc ttt                               33

<210> SEQ ID NO 11
<211> LENGTH: 33
<212> TYPE: DNA
<213> ORGANISM: Homo sapiens

<400> SEQUENCE: 11
aaaaaaatcg atatgagctt gttaaatcaa cat                               33

<210> SEQ ID NO 12
<211> LENGTH: 33
<212> TYPE: DNA
<213> ORGANISM: Homo sapiens

<400> SEQUENCE: 12
aaaaaaggat ccttagctct cctggatgta ttt                               33

<210> SEQ ID NO 13
<211> LENGTH: 33
<212> TYPE: DNA
<213> ORGANISM: Homo sapiens

<400> SEQUENCE: 13
aaaaaaatcg atatgcaagc attggcaaag cga                               33

<210> SEQ ID NO 14
<211> LENGTH: 33
<212> TYPE: DNA
<213> ORGANISM: Homo sapiens

<400> SEQUENCE: 14
aaaaaaggat ccttaaactc ccaaagcagc acg                               33

<210> SEQ ID NO 15
<211> LENGTH: 33
<212> TYPE: DNA
<213> ORGANISM: Homo sapiens

<400> SEQUENCE: 15
aaaaaaatcg atatgtccta catatgttct caa                               33

<210> SEQ ID NO 16
<211> LENGTH: 9
<212> TYPE: PRT
<213> ORGANISM: Homo sapiens

<400> SEQUENCE: 16

Ser Tyr Ile Cys Ser Gln Gln Asp Thr
 1               5
```